United States Patent
Davison et al.

(10) Patent No.: US 9,361,410 B2
(45) Date of Patent: Jun. 7, 2016

(54) SURGICAL GUIDES FROM SCANNED IMPLANT DATA

(71) Applicant: DePuy Synthes Products, Inc., Raynham, MA (US)

(72) Inventors: Andrew Charles Davison, West Chester, PA (US); John Wayne Mest, West Chester, PA (US)

(73) Assignee: DePuy Synthes Products, Inc., Raynham, MA (US)

(*) Notice: Subject to any disclaimer, the term of this patent is extended or adjusted under 35 U.S.C. 154(b) by 11 days.

(21) Appl. No.: 13/792,746

(22) Filed: Mar. 11, 2013

(65) Prior Publication Data

US 2014/0149095 A1 May 29, 2014

Related U.S. Application Data

(60) Provisional application No. 61/645,890, filed on May 11, 2012, provisional application No. 61/642,063, filed on May 3, 2012, provisional application No. 61/699,938, filed on Sep. 12, 2012.

(51) Int. Cl.

| A61B 17/17 | (2006.01) |
|---|---|
| G06F 17/50 | (2006.01) |
| A61B 17/15 | (2006.01) |
| A61B 19/00 | (2006.01) |
| A61F 2/46 | (2006.01) |

(52) U.S. Cl.
CPC ............ *G06F 17/5009* (2013.01); *A61B 17/15* (2013.01); *A61B 17/17* (2013.01); *A61B 17/1728* (2013.01); *A61B 17/1739* (2013.01); *A61B 19/50* (2013.01); *A61B 17/176* (2013.01); *A61F 2002/4649* (2013.01)

(58) Field of Classification Search
USPC .................................. 703/1, 2; 433/3; 623/16
See application file for complete search history.

(56) References Cited

U.S. PATENT DOCUMENTS

| 5,042,983 A | 8/1991 | Rayhack |
|---|---|---|
| 5,098,383 A | 3/1992 | Hemmy et al. |
| 5,176,685 A | 1/1993 | Rayhack |
| 5,413,579 A | 5/1995 | Toit |
| 5,601,563 A | 2/1997 | Burke et al. |
| 5,860,981 A | 1/1999 | Bertin et al. |
| 5,876,204 A | 3/1999 | Day et al. |
| 5,916,220 A | 6/1999 | Masini |
| 6,007,537 A | 12/1999 | Burkinshaw et al. |

(Continued)

FOREIGN PATENT DOCUMENTS

| EP | 0468192 | 9/1996 |
|---|---|---|
| EP | 1216666 | 6/2002 |

(Continued)

OTHER PUBLICATIONS

International Patent Application No. PCT/US2013/030139: International Search Report dated Aug. 6, 2013, 19 pages.

(Continued)

*Primary Examiner* — Thai Phan
(74) *Attorney, Agent, or Firm* — Baker & Hostetler LLP

(57) ABSTRACT

A method of making a patient specific surgical guide includes obtaining a virtual model of a fixation member, and virtually designing a guide that defines at least one hole that corresponds to a hole of the virtual model of the fixation member.

30 Claims, 15 Drawing Sheets

(56) References Cited

U.S. PATENT DOCUMENTS

| | | | |
|---|---|---|---|
| 6,077,266 A | 6/2000 | Medoff | |
| 6,110,177 A | 8/2000 | Ebner et al. | |
| 6,978,188 B1 | 12/2005 | Christensen | |
| 7,621,919 B2 | 11/2009 | Williams, III et al. | |
| 7,758,345 B1 | 7/2010 | Christensen | |
| 8,086,336 B2 | 12/2011 | Christensen | |
| 8,177,822 B2 | 5/2012 | Medoff | |
| 8,439,926 B2 | 5/2013 | Bojarski et al. | |
| 8,725,465 B2 * | 5/2014 | Hultgren et al. | 703/1 |
| 8,775,133 B2 * | 7/2014 | Schroeder | 703/1 |
| 2002/0082604 A1 | 6/2002 | Abdelgany et al. | |
| 2002/0138078 A1 | 9/2002 | Chappuis | |
| 2004/0034361 A1 | 2/2004 | Dalton | |
| 2004/0097946 A1 | 5/2004 | Dietzel et al. | |
| 2005/0043835 A1 | 2/2005 | Christensen | |
| 2005/0133955 A1 | 6/2005 | Christensen | |
| 2008/0195240 A1 | 8/2008 | Martin et al. | |
| 2008/0221569 A1 | 9/2008 | Moore et al. | |
| 2008/0275452 A1 | 11/2008 | Lang et al. | |
| 2009/0047165 A1 | 2/2009 | Syvanen et al. | |
| 2009/0082774 A1 | 3/2009 | Oti et al. | |
| 2009/0087276 A1 | 4/2009 | Rose | |
| 2009/0088758 A1 | 4/2009 | Bennett | |
| 2009/0092948 A1 | 4/2009 | Gantes | |
| 2010/0137873 A1 | 6/2010 | Grady, Jr. et al. | |
| 2010/0152782 A1 | 6/2010 | Stone et al. | |
| 2010/0168752 A1 | 7/2010 | Edwards | |
| 2010/0168753 A1 | 7/2010 | Edwards et al. | |
| 2010/0169057 A1 * | 7/2010 | Hultgren et al. | 703/1 |
| 2010/0216083 A1 * | 8/2010 | Grobbee | 433/3 |
| 2010/0262150 A1 | 10/2010 | Lian | |
| 2010/0292963 A1 * | 11/2010 | Schroeder | 703/1 |
| 2010/0324558 A1 | 12/2010 | Bickley et al. | |
| 2011/0008754 A1 | 1/2011 | Bassett et al. | |
| 2011/0092804 A1 | 4/2011 | Schoenefeld et al. | |
| 2011/0144698 A1 | 6/2011 | Buchbinder et al. | |
| 2012/0022604 A1 | 1/2012 | Polley et al. | |
| 2012/0029574 A1 | 2/2012 | Furrer et al. | |
| 2012/0109135 A1 | 5/2012 | Bailey | |
| 2012/0130686 A1 | 5/2012 | Graumann | |
| 2012/0141034 A1 | 6/2012 | Iannotti et al. | |
| 2012/0150243 A9 | 6/2012 | Crawford et al. | |
| 2012/0261848 A1 | 10/2012 | Haraszati | |
| 2012/0276509 A1 | 11/2012 | Iannotti et al. | |
| 2012/0289965 A1 | 11/2012 | Gelaude et al. | |
| 2012/0303131 A1 | 11/2012 | Chana | |
| 2013/0072988 A1 | 3/2013 | Hulliger | |

FOREIGN PATENT DOCUMENTS

| | | |
|---|---|---|
| EP | 1854611 | 11/2007 |
| EP | 1808137 | 4/2010 |
| EP | 2208470 | 7/2010 |
| EP | 2062224 | 8/2010 |
| FR | 2847453 | 5/2004 |
| WO | WO 2004/039266 | 5/2004 |
| WO | WO 2005/032790 | 4/2005 |
| WO | WO 2011/070367 | 6/2011 |
| WO | WO 2011/071611 | 6/2011 |
| WO | WO 2011/080260 | 7/2011 |
| WO | WO 2011/103689 A1 | 9/2011 |
| WO | WO 2012/027574 | 3/2012 |

OTHER PUBLICATIONS

U.S. Appl. No. 13/792,849, filed Mar. 11, 2013, Davison et al.

U.S. Appl. No. 13/801,244, filed Mar. 13, 2013, Furrer et al.

Cevidanes et al., "Three-Dimensional Surgical Simulation", Am. J. Orthod. Dentofacial. Orthop., Sep. 2010, 138(3), 361-371.

Chapuis et al., "A New System for Computer-Aided Preoperative Planning and Intraoperative Navigation During Corrective Jaw Surgery", IEEE Trans. Inf. Technol. Biomed., May 2007, 11(3), 274-287.

DePuy Orthopaedics, Inc., "TruMatch Personalized Solutions", Oct. 27, 2011, 2 pages.

International Patent Application No. PCT/US2013/030131: International Search Report dated Jun. 25, 2013, 11 pages.

International Patent Application No. PCT/US2013/030139: Invitation to Pay Additional Fees dated Jun. 10, 2013, 5 pages.

Lubbers et al., "Surgical Navigation in Craniomaxillofacial Surgery: Expensive Toy or Useful Tool? A Classification of Different Indications", J. Oral Maxillofac. Surg., Jan. 2011, 69(1), 300-308.

Mavili et al., "Use of Three-Dimensional Medical Modeling Methods for Precise Planning of Orthognathic Surgery", J. Craniofac. Surg., Jul. 2007, 18(4), 740-747.

Olszewski et al., "Innovative Procedure for Computer-Assisted Genioplasty: Three-Dimensional Cephalometry, Rapid-Prototyping Model and Surgical Splint", Int. J. Oral Maxillofac. Surg., Jul. 2010, 39(7), 721-724.

U.S. Appl. No. 13/900,817, filed May 23, 2013, Davison et al.

Klein et al., A Computerized Tomography (CT) Scan Appliance for Optimal Presurgical and Preprosthetic Planning of the Implant Patient, Practical Periodontics & Aesthetic Dentistry, vol. 5, No. 6, 1993, 33-39.

International Patent Application No. PCT/US2013/059226; International Search Report dated Dec. 2, 2013, 10 pages.

* cited by examiner

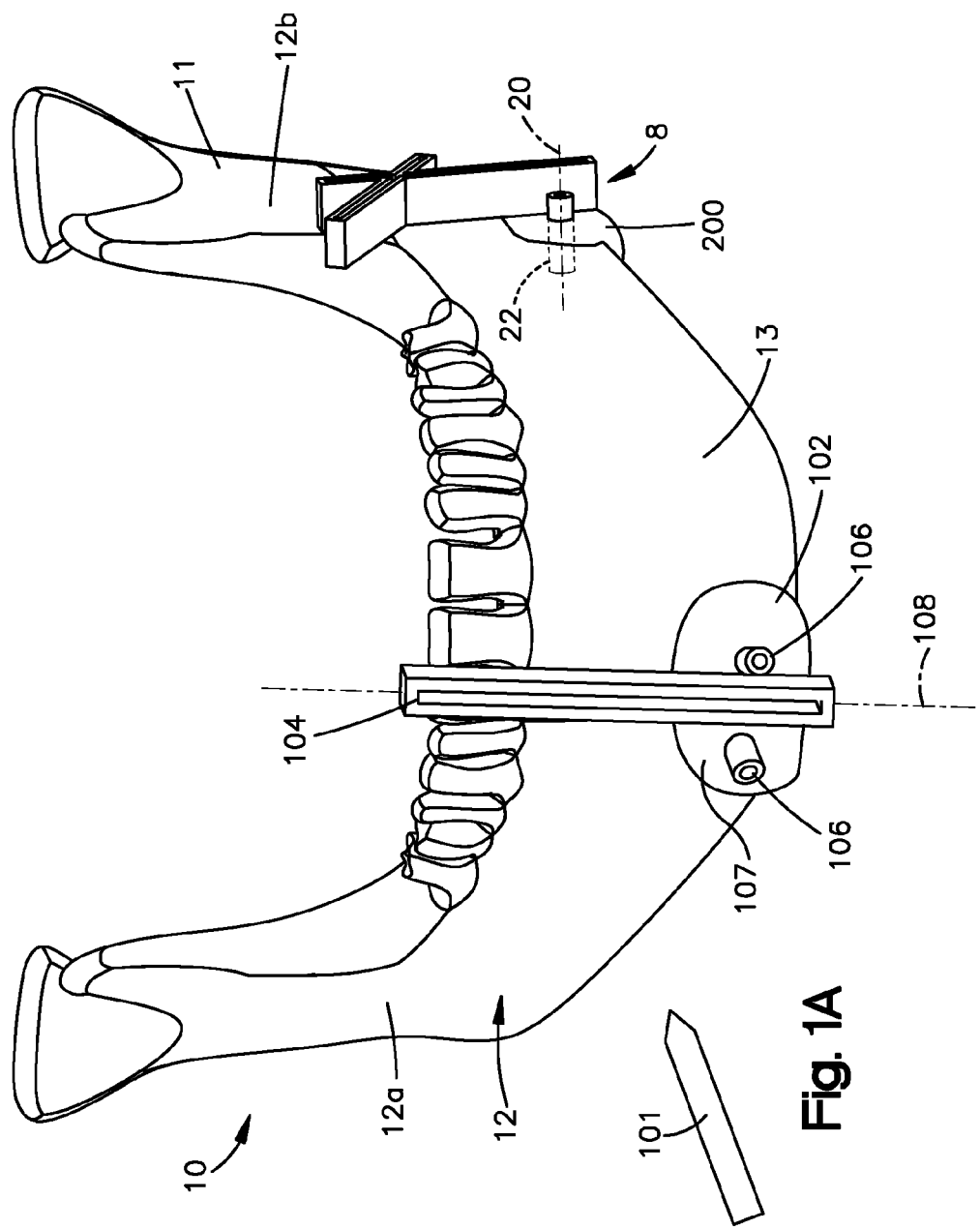

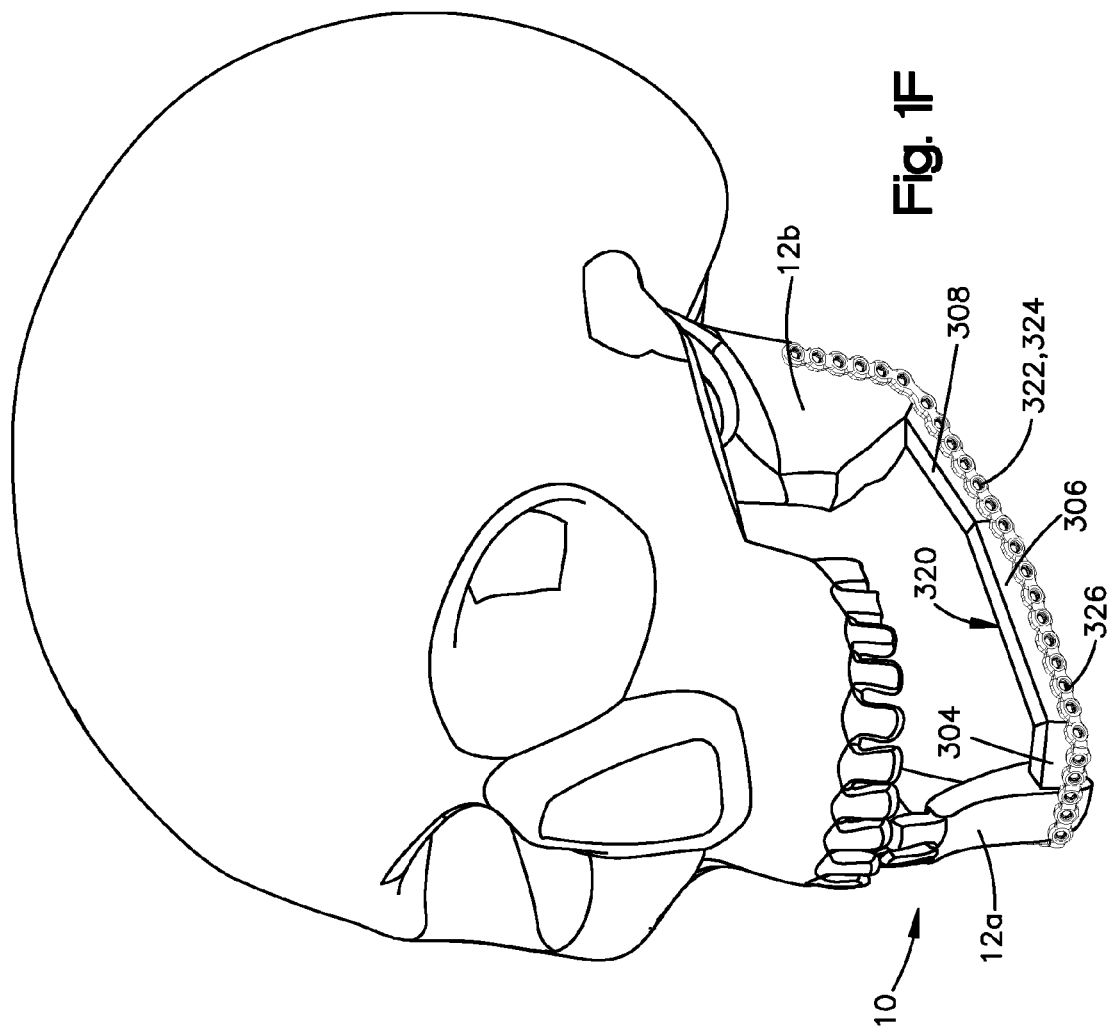

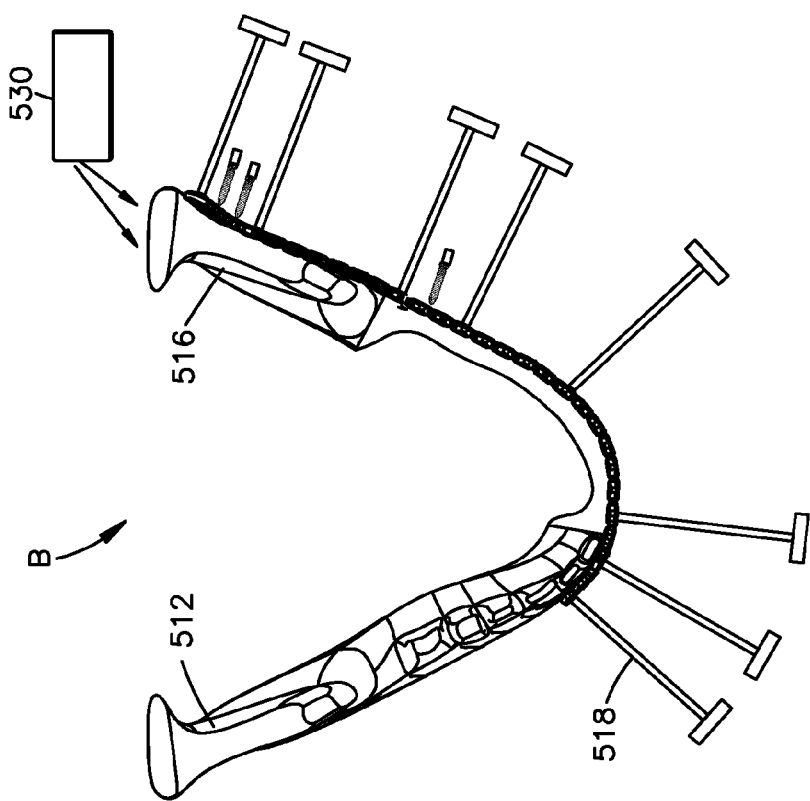
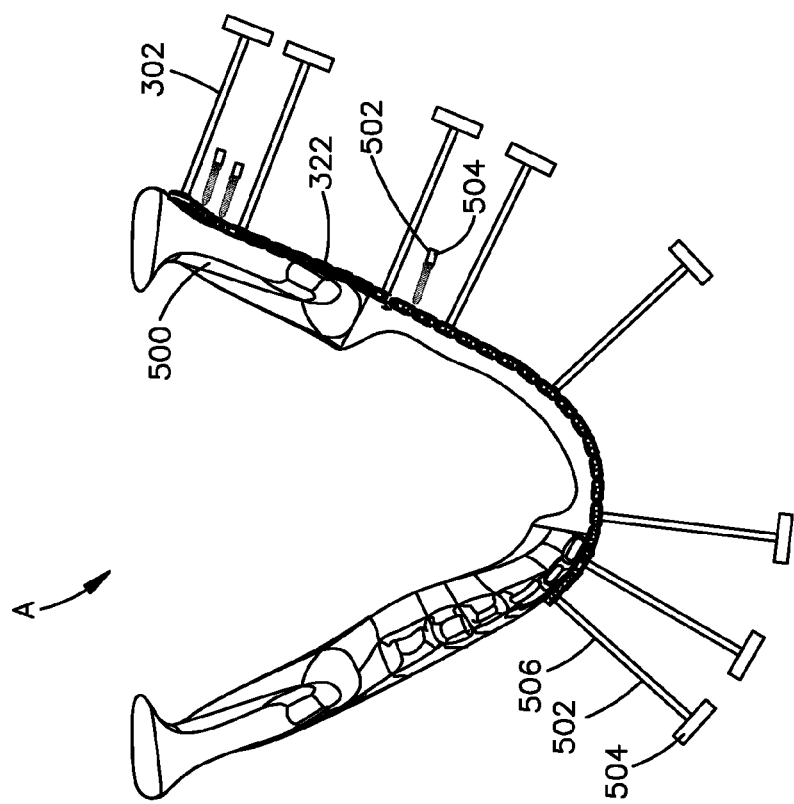
Fig. 3A
Fig. 3B

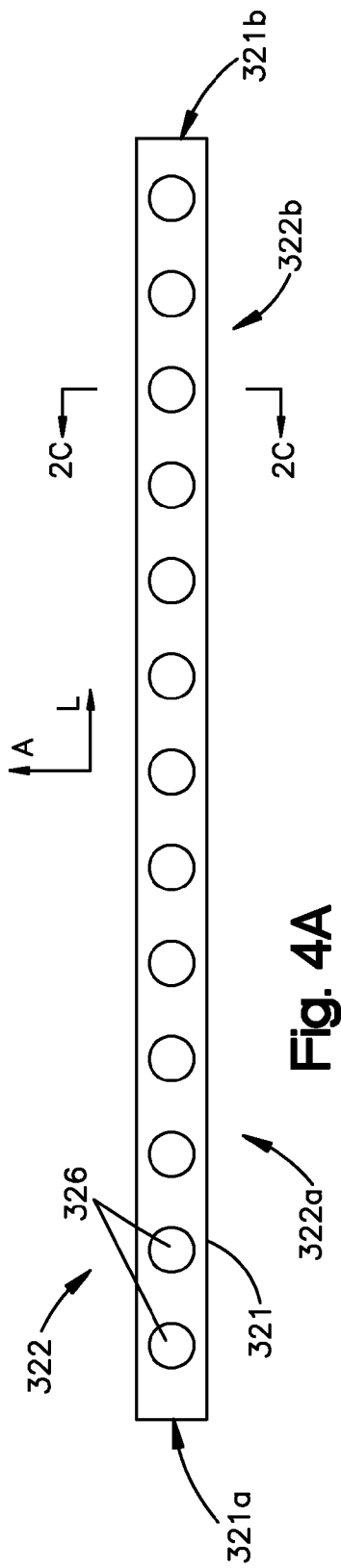
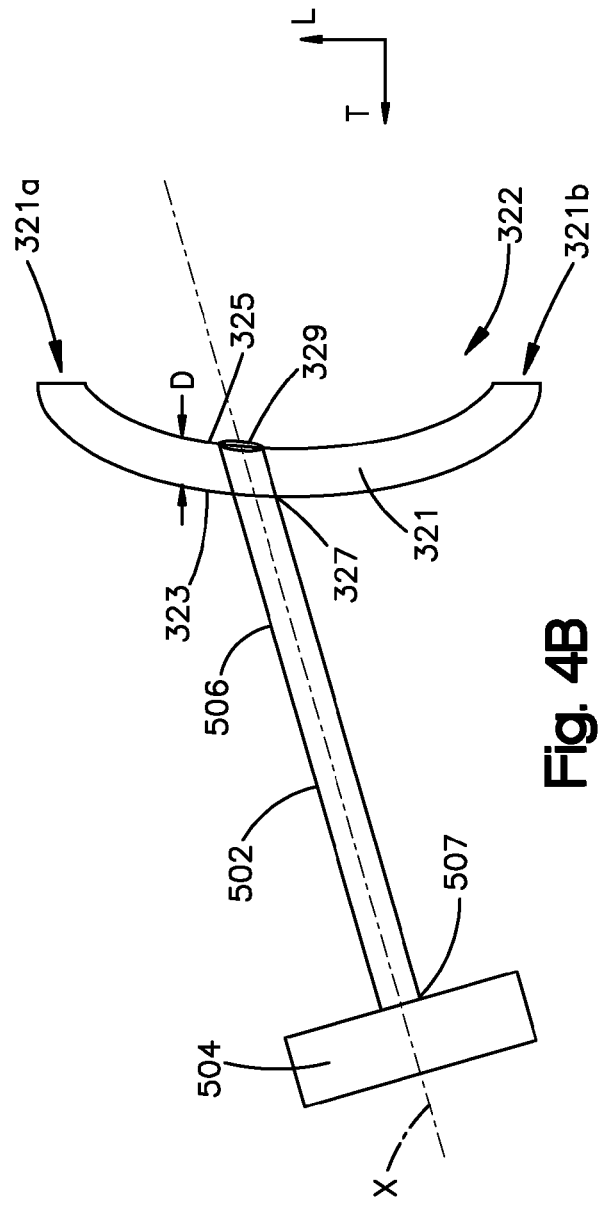

SURGICAL GUIDES FROM SCANNED IMPLANT DATA

CROSS REFERENCE

This application claims the benefit of U.S. Provisional Patent Application Ser. No. 61/645,890 filed May 11, 2012, U.S. Provisional Patent Application Ser. No. 61/642,063 filed May 3, 2012, and also U.S. Provisional Patent Application Ser. No. 61/699,938 filed Sep. 12, 2012, the entire disclosures of which are hereby incorporated by reference into this patent application for all purposes.

TECHNICAL FIELD

The present disclosure generally relates to apparatus and methods for manufacturing a surgical guide, and more particularly, to apparatus and methods for manufacturing a patient specific resection guide.

BACKGROUND

Many surgical procedures require accurate cuts of bone. For example, in mandibular reconstruction surgery, deficient or infectious portions of the mandible may be removed from the patient and replaced with bone graft. In some instances, a surgeon performing mandibular reconstruction surgery typically makes several cuts on the mandible to properly fit a bone graft. To make an accurate cut, the surgeon may use a resection guide to guide the motion of the resection tool toward the bone. The resection guide can also be used to cut a bone portion from other anatomic locations of the patient in order to harvest bone grafts.

As discussed above, resection guides are typically used to make accurate cuts on the patient's anatomy. Although many resection guides have been developed over the years, it is still desirable to produce resection guides that are specifically designed for a particular patient in order to enhance cutting accuracy.

SUMMARY

The present disclosure relates to methods of making a patient specific surgical guide that is configured to guide a movement of a tool toward a tissue body. In an embodiment, the method includes the following steps: (1) obtaining a virtual three-dimensional model of a fixation member, the obtained virtual three-dimensional model of the fixation member having a planned post-operative shape and defining at least one hole that is configured to receive a fastener; (2) processing the virtual three-dimensional model of the fixation member so as to couple the virtual three-dimensional model of the fixation member to a first virtual three-dimensional model of the tissue body, the first virtual three-dimensional model of the tissue body defining a first region, such that a central axis of the at least one hole is substantially aligned with a first target location of the first region; (3) creating a virtual three-dimensional model of a guide that defines at least one hole; and (4) processing the virtual three-dimensional model of the guide so as to couple the virtual three-dimensional model of the guide to a second virtual three-dimensional model of the tissue body having a second region that is substantially identical to the first region, such that a central axis of the at least one hole is substantially aligned with a second target location of the second virtual three-dimensional model of the tissue body, wherein the second target location is positioned identically with respect to the first target location relative to the respective first and second virtual three-dimensional models of the tissue body.

In an embodiment, the method includes the following steps: (1) processing a virtual three-dimensional model of a fixation member so as to couple the virtual three-dimensional model of the fixation member to a first virtual three-dimensional model of the tissue body, the first virtual three-dimensional model of the tissue body defining a first region, such that a central axis of the at least one hole is substantially aligned with a first target location of the first region; (2) creating a virtual three-dimensional model of a guide that defines at least one hole; and (3) processing the virtual three-dimensional model of the guide so as to couple the virtual three-dimensional model of the guide to a second virtual three-dimensional model of the tissue body having a second region that is substantially identical to the first region, such that a central axis of the at least one hole is substantially aligned with a second target location of the second virtual three-dimensional model of the tissue body, wherein the second target location is positioned identically with respect to the first target location relative to the respective first and second virtual three-dimensional models of the tissue body.

In an embodiment, the method includes the following steps: (1) obtaining a virtual three-dimensional model of the tissue body; (2) identifying on the virtual three-dimensional model of the tissue body a first region and a second region; (3) obtaining a virtual three-dimensional model of a fixation member, the obtained virtual three-dimensional model of the fixation member having a planned post-operative shape and defining at least one first hole that is configured to receive a fastener; (4) processing the virtual three-dimensional model of the fixation member so as to couple the virtual three-dimensional model of the fixation member to the virtual three-dimensional model of the tissue body, such that a central axis of the at least one first hole is substantially aligned with a first target location of the second region; (5) creating a virtual three-dimensional model of a resection guide that defines at least a pair of cutting guides and at least one second hole; and (6) processing the virtual three-dimensional model of the resection guide so as to couple the virtual three-dimensional model of the resection guide to a virtual three-dimensional model of a graft portion disposed between the cutting guides, the graft portion sized to fit in the second region, such that a central axis of the at least one second hole is substantially aligned with a second target location of the three-dimensional model of the graft portion, wherein the second target location substantially coincides with respect to the first target location when the graft portion is positioned in the second region.

BRIEF DESCRIPTION OF THE DRAWINGS

The foregoing summary, as well as the following detailed description of the preferred embodiments of the application, will be better understood when read in conjunction with the appended drawings. For the purposes of illustrating the surgical instruments and methods of the present application, there is shown in the drawings preferred embodiments. It should be understood, however, that the application is not limited to the specific embodiments and methods disclosed, and reference is made to the claims for that purpose. In the drawings:

FIG. 1A is a front elevation view of a resection guide coupled to a patient's tissue body;

FIG. 1F is a perspective view of a fixation member coupled to the patient's tissue body shown in FIG. 1A;

FIG. 3A illustrates a physical model of a tissue body in a pre-operative condition and a fixation member applied to the physical model, according to an embodiment of the disclosure;

FIG. 3B illustrates a virtual three dimensional model of the physical model and fixation member shown FIG. 3B;

FIG. 4A is a front elevation view of the fixation member shown in FIG. 1F;

FIG. 4B is a top view of the a fixation member rand a marker shown in FIG. 4A, according to an embodiment of the disclosure;

DETAILED DESCRIPTION OF ILLUSTRATIVE EMBODIMENTS

Figure 1B:
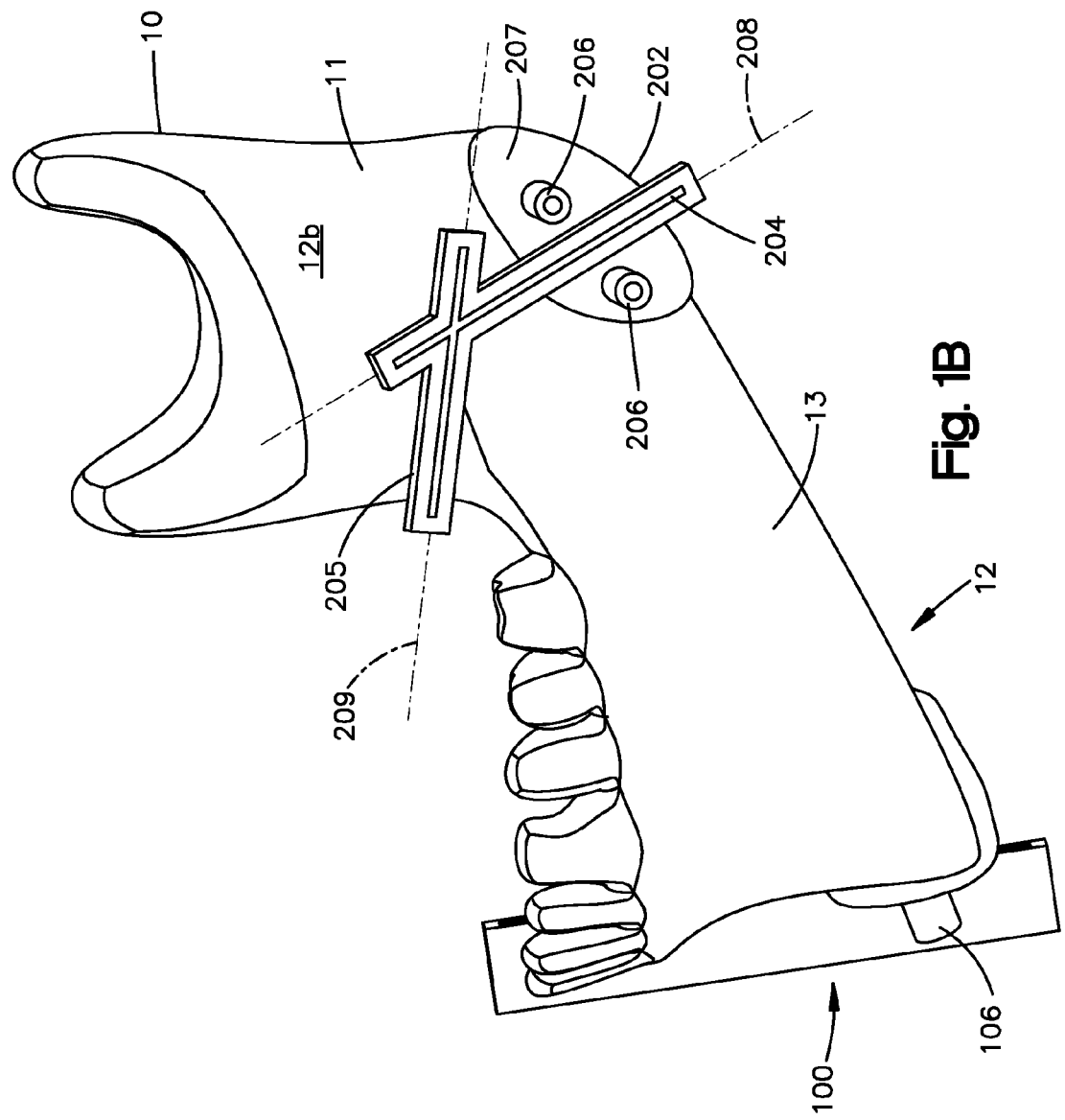
FIG. 1B is a side elevation view of the resection guide shown in FIG. 1A.

Certain terminology is used in the following description for convenience only and is not limiting. The words "right", "left", "lower" and "upper" designate directions in the drawings to which reference is made. The words "proximally" and "distally" refer to directions toward and away from, respectively, the surgeon using the surgical device. The words, "anterior", "posterior", "superior", "inferior" and related words and/or phrases designate preferred positions and orientations in the human body to which reference is made and are not meant to be limiting. The terminology includes the above-listed words, derivatives thereof, and words of similar import.

Figure 1C:
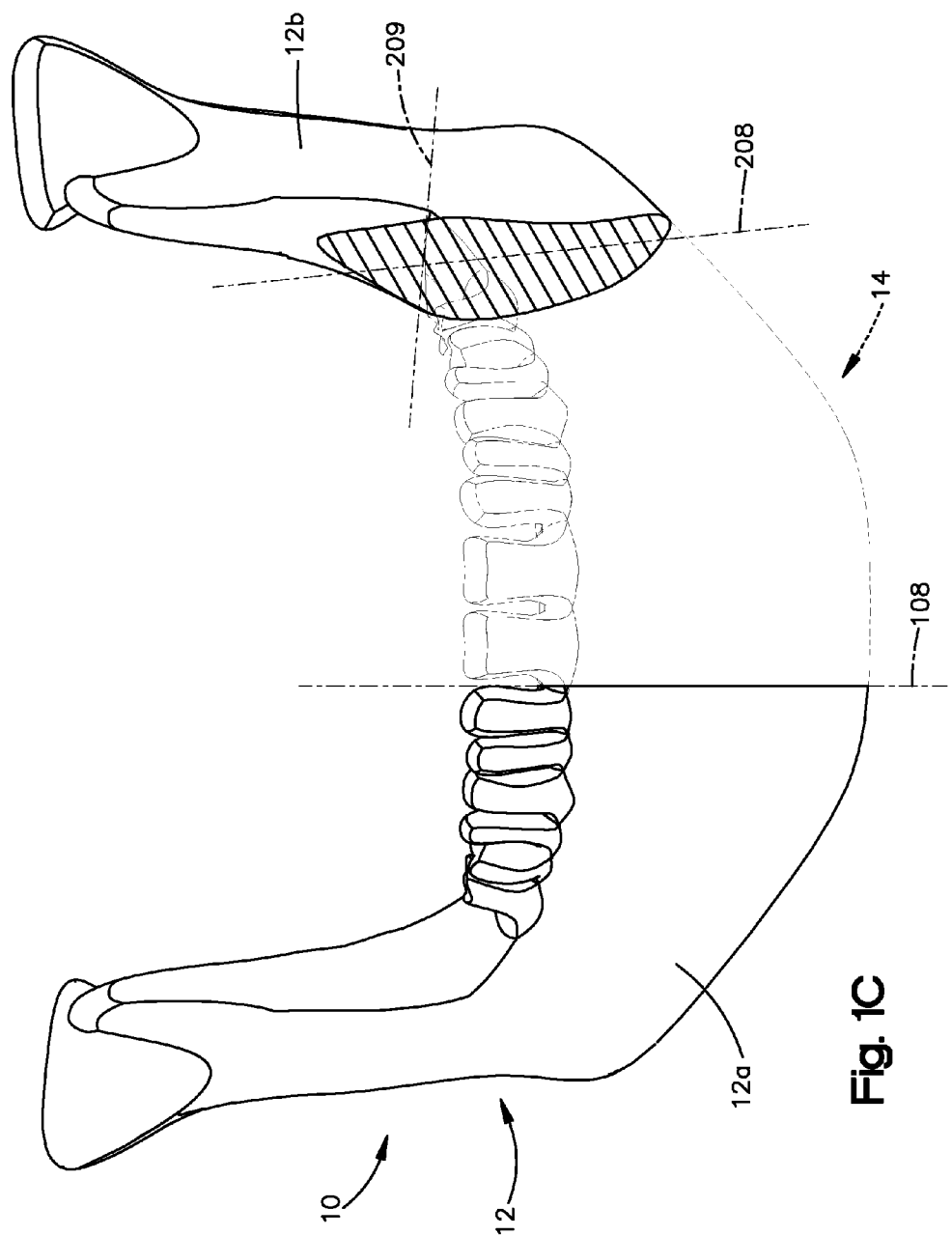
FIG. 1C is a front elevation view of the tissue body shown in FIG. 1A after a tissue portion has been removed from the patient.

With reference to FIGS. 1A-1C, a surgical system 8 can include one or more resection guides 100 and 200 that can be coupled to a tissue body 10 to guide one or more tools 101 toward the tissue body 10 in order to prepare the tissue body 10 for receiving a graft. For instance the resection guides 100 and 200 can guide a tool 101 that cuts the tissue body 10 so as to create a void 14 (FIG. 1C) in the tissue body 10. The tissue body 10 can define spaced apart first and second tissue portions 12a and 12b. The first and second tissue portions 12a and 12b can be any particular portions or segments of the tissue body and are used herein to refer to tissue portions that define the void 14. Further, the resection guides 100 and 200 can be used to guide a drill bit that form anchoring locations 22 (FIG. 1B), for instance bores or holes, in the tissue body 10. Anchoring locations are used to allow an anchor or screw to couple a bone fixation member, such as plate, to the tissue body 10 as detailed below. It should be appreciated that the cutting tool 101 may be a saw, blade, a drill bit, or any other tool capable of cutting or otherwise preparing tissue. As used herein, the tissue body 10 can include a patient's bone, such as the mandible 12, and can include the first and second tissue portions 12a and 12b. The tissue body 10 can also include anatomical tissue, synthetic tissue, or both. Although the drawings illustrate a mandible 12, the tissue body 10 can be other parts of the patient's anatomy such as a maxilla.

Referring to FIG. 1A, the resection guide 100 is configured to be coupled to the tissue body 10 and can include a resection guide body 102 that is configured to abut at least a portion of the tissue body 10, for instance tissue portion 12a. The resection guide body 102 can define an inner surface (not shown) that is contoured to match the contour of a particular outer surface of the tissue body 10 so that the resection guide 100 can only fit over the that particular outer surface of the tissue body 10. The resection guide 100 can define one or more slots 104 that are configured and sized to receive the cutting tool 101 therein. The slot 104 can extend through the resection guide body 102, and can be elongate along a first resection axis 108. The tissue body 10 can be cut by inserting the cutting tool 101 through the slot 104 when the resection guide 100 is coupled to the tissue body 10. In particular, the slot 104 guides the movement of the cutting tool 101 toward the tissue body 10 along the first resection axis 108.

In addition to the slot 104, the resection guide 100 can further include one or more drill holes 106 that extend through the resection guide body 102. Each of the drill holes 106 is configured and sized to receive a drill bit or any other suitable tool capable of making holes into and/or through the tissue body 10. The drill holes 106 can be elongate along an anchoring location axis 20. The anchoring location axis 20 thus extends through the drill hole 106 into alignment with then anchoring location 22, for instance a hole or bore, formed in the tissue body by the drill bit inserted through the drill hole 106. The anchoring location 22 is configured and sized to receive an anchor or fastener.

The resection guide 100 can further define one or more fastener holes 107 that are configured and sized to receive a fastener, such as a pin, a wire, or a screw therethrough. Each of the fastener holes 107 extends through the resection guide body 102 and is configured to guide the movement of the fastener through the resection guide body 102 in order to temporarily couple the resection guide 100 to the tissue body 10.

When resection guide 100 is coupled to the tissue body 10, the cutting tool 101 can be inserted through the slot 104 and into the tissue body 10 to make a cut on the tissue body 10 at the desired anatomical location. Further, the drill bit can be inserted through the drill holes 106 to form the anchoring locations in the tissue body 10. The fasteners inserted through the fastener holes 107 can then be withdrawn from the tissue body 10 and the resection guide body 102 to decouple the resection guide 100 from the tissue body 10. Although the present disclosure mostly refers to resection guides, any of the resection guides described herein may alternatively be positioning guides, drill guides, or any other guide defining at least one hole that is configured to receive a cutting tool such as a drill bit.

With reference to FIG. 1B, the resection guide 200 is configured to be coupled to the tissue body 10 to guide the movement of one or more tools 101 toward the tissue body 10 in order to prepare the tissue body 10. The resection guide 200 is configured similarly to the resection guide 100, however, the resection guide 200 can be coupled to the tissue body 10 at a location spaced from the resection guide 100. The resection guides 100 and 200 can be used to guide a tool 101 to resect tissue from the tissue body 10 so as to create the void 14 (FIG. 1C). The resection guide 200 can include a resection guide body 202 that is configured to abut at least a portion of the tissue body 10, for instance tissue portion 12b. The resection guide body 202 can define an inner surface that is contoured to match the contoured of a particular outer surface of the tissue body 10 so that the resection guide 200 can only fit over the that particular outer surface of the tissue body 10. The resection guide 200 can define one or more slots 204 that are configured to receive the cutting tool 101. In the depicted embodiment, the resection guide 200 can define a first slot 204 and a second slot 205. Each of the first slot 204 and the second slot 205 extends through the resection guide body 202, and each can be configured to receive the cutting tool 101. The first slot 204 can be elongate along a first resection axis 208 such that the first slot 204 can guide the movement of the cutting tool 101 into the tissue body 10 along the first resection axis 208. The second slot 205 can be elongate along a second resection axis 209 such that the second slot 205 can guide the movement of the cutting tool 101 into the tissue body 10. The first resection axis 208 can be oriented at an oblique angle relative to the second resection axis 209. In operation, the cutting tool 101 can be inserted through slot 204 and 205 and into the tissue body 10 to cut the tissue body 10.

In addition to the first slot 204 and the second slot 205, the resection guide 200 can define one or more drill holes 206 that extend through the resection guide body 202. Each of the drill holes 206 is configured and sized to receive a drill bit or any other suitable tool capable of making holes into and/or through the tissue body 10. The drill holes 206 can be elongate along an anchoring location axis 24. The anchoring location axis 24 thus extends through the drill hole 106 into alignment with anchoring location 22, for instance a hole or bore, formed in the tissue body by the drill bit inserted through the drill hole 206. The anchoring location 22 is configured and sized to receive an anchor or fastener.

The resection guide 200 can further define one or more fastener holes 207 that extend through the resection guide body 202 that are configured and sized to receive a fastener, such as a pin, a wire, or a screw, that is used to temporarily couple the resection guide 200 to the tissue body 10. Once the resection guide 200 is coupled to the tissue body 10, the cutting tool 101 can be inserted through the slot 204 and into the tissue body 10 to make a cut on the tissue body 10 at the desired anatomical location. Further, the cutting tool 101 can be inserted through the slot 205 and into the tissue body 10 to make a cut on the tissue body 10 at the desired anatomical location. A drill bit can inserted through the drill guide holes 206 to form an anchoring location 22 in the tissue body 10. When cuts have been made on the tissue body 10 along the resection axes 108, 208, and 209, a portion of the tissue body 10 can be removed from the patient. The fasteners inserted through the fastener holes 207 can be withdrawn from the tissue body 10 to decouple the resection guide 200 from the tissue body 10.

With reference to FIG. 1C, as discussed above, cuts can be made on the tissue body 10 along the resection axes 108, 208, and 209 to allow removal of a tissue portion from the tissue body 10, thereby defining a void 14 in the tissue body 10. The void 14 extends between the cut, exposed surfaces of the tissue portion 12a and 12b. The removed tissue portion can be damaged or diseased tissue. The void 14 of the tissue body 10 can be filled with the graft, and the graft coupled to the tissue portions 12a and 12b with the bone fixation element, or plate, as discussed in detail below.

Figure 1D:
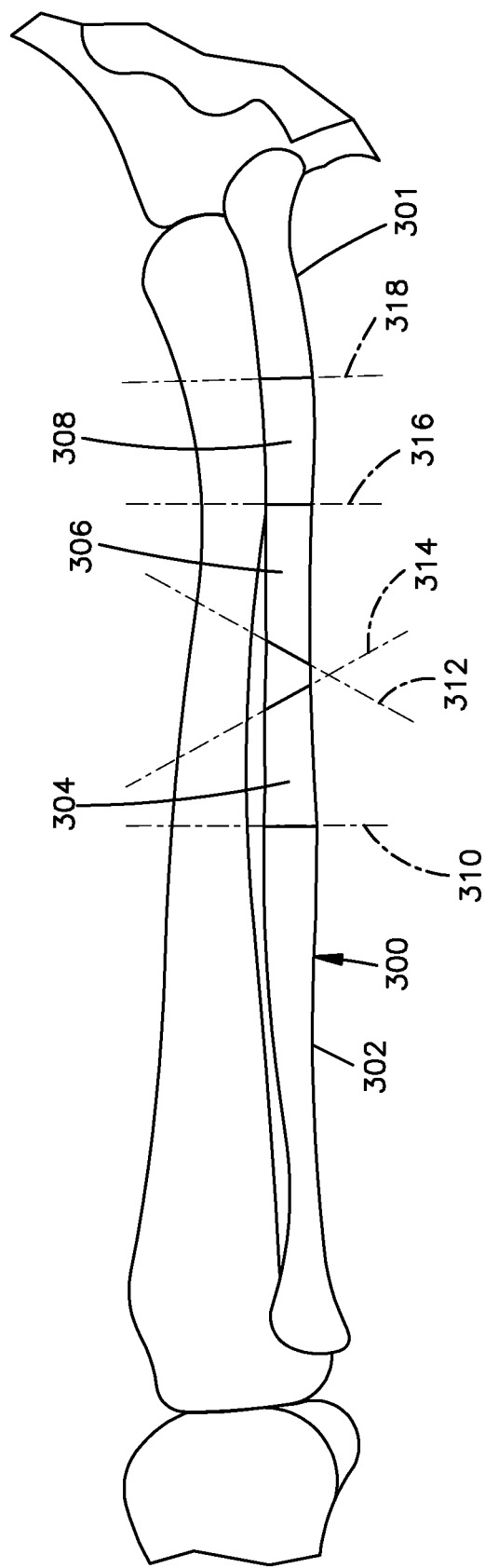
FIG. 1D is a side elevation view of a virtual three-dimensional model of a graft source.
Figure 1E:
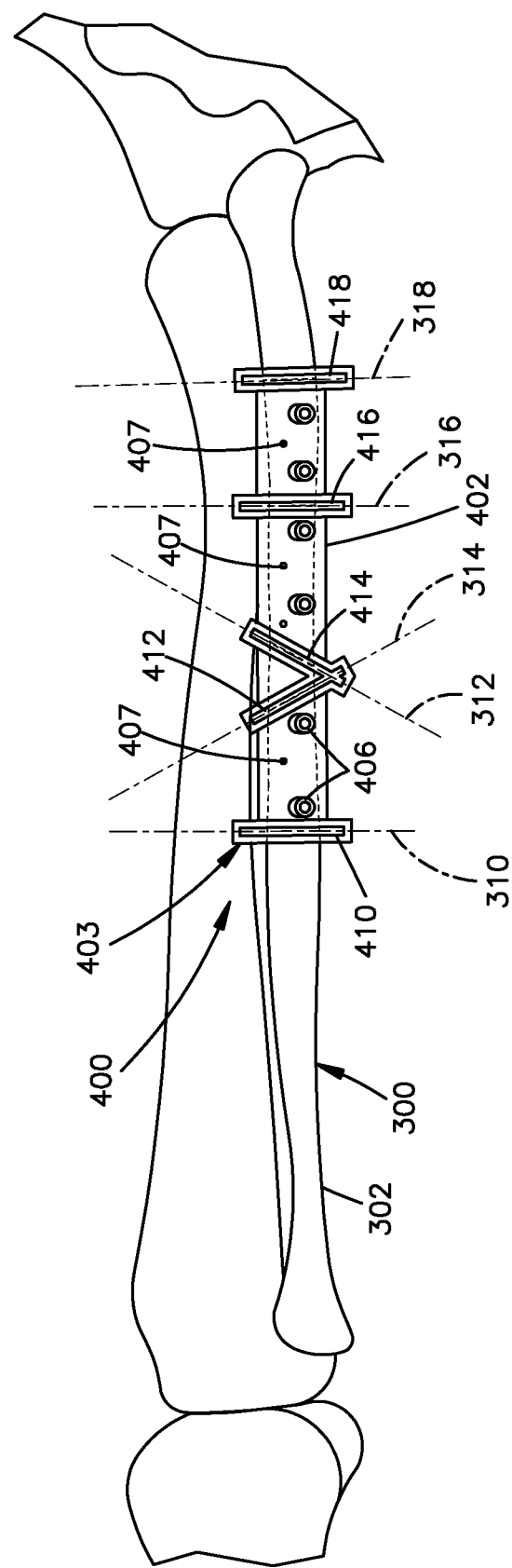
FIG. 1E is a side elevation view of another resection guide coupled to the graft source.

With reference to FIGS. 1D-E, as discussed above, the removed tissue portion can be replaced with the graft, such as graft 320 (FIG. 1F). The graft can be harvested from any suitable graft source 300, such as a vascularized bone graft source. Further, the graft can be an autologous graft. Examples of suitable graft sources include, but are not limited to, the scapula, hip, rib, forearm, among others. The graft source 300 can also be a fibula 302. Regardless of the kind of graft source selected, the graft source 300 can be cut at appropriate locations and orientation to obtain a graft that properly fits in the void 14 (FIG. 1C) defined by the cut exposed surfaces of the tissue portions 12a and 12b. To define size and shape of the desired graft, a virtual three-dimensional model 301 of the graft source 300 can be obtained to determine the appropriate location and orientation of the cuts to be made to harvest a graft from the graft source 300. The virtual three-dimensional model 301 of the graft source 300 can be obtained by scanning the graft source 300 using any suitable technology such as x-ray computed tomography (CT), or any suitable mapping technology for instance, laser, optical, CT, magnetic resonance imaging (MRI) and coordinate measuring machines. In an embodiment, an imaging machine, such as CT scan machine, can be used to scan the graft source 300. The imaging machine can include or be in electronic communication with a computer, such a computer 530, that includes a computer memory in electronic communication with a processor. The computer 530 can be any computing device and can include a smart phone, tablet or any other computer. The data obtained by scanning the graft source 300 can transmitted to or stored in the computer memory. The scanned data can be processed, via the processor, and in accordance with software instructions running on the computer 530, to create the virtual three-dimensional model 301 of the graft source 300. Alternatively, the scanned data can be downloaded or transferred wirelessly or via a hardwire connection over an electronic communications network to a different computing device at a location that is remote from the imaging machine, in order to create the virtual three-dimensional model 301 of the graft source 300.

When the virtual three-dimensional model 301 of the graft source 300 has been obtained, the surgical operation can be planned. The surgical operation can be planned using any suitable software program that is configured to process, edit and manipulate data that is representative of the image of the scanned graft source, for instance scanned image data. The software operate over networked computing architecture that includes host and client computing devices. Further, the software can be a web based application configured to process instructions based on inputs from a graphical user interface running on a computer, for instance computer 530. In an embodiment, one suitable software program configured to process, manipulate and or edit images or image data, is sold or licensed under the trademark PROPLAN CMF® by Synthes. PROPLAN CMF® can be used to process and manipulate the virtual three-dimensional model 301.

The graft 320 that replaces the removed tissue portion should be configured and sized to fit properly in the void 14

(FIG. 1C). For instance, a plurality of graft portions 304, 306, and 308 can be harvested from the graft source 300 and then interconnected to from a complete graft for insertion in the void 14. As such, resection axes can be defined as so the form the plurality of graft portions 305, 306, and 308. Using the virtual three-dimensional model 301 of the graft source 300, the resection can be planned via the computer running software that is configured to process, manipulate and edit images, such as the scanned image data described above. The user can input instructions that causes the processor to carry out the desired edits or manipulations to the virtual three-dimensional model 301 of the graft source 300. The user can determine the location and the orientation of the resections to be made on the graft source 300 to obtain graft portions 304, 306, and 308 that can later be interconnected to form the graft 320. To harvest the graft portions 304, 306, and 308, the user can determine that cuts have to be made along the resection axes 310, 312, 314, 316, and 318. It should be appreciated that patient anatomy and shape and size of the removed tissue portion, resections can be made along other resection axes to form the properly sized graft portions.

With continuing reference to FIGS. 1D-E, after planning the desired resections to be made on the graft source 300 using the virtual three-dimensional model 301 in the computer, the resection guide 400 configured in accordance with the planned surgical procedure and manufacturing using rapid production technology as described below can be placed on the graft source 300 to guide the movement of the cutting tool 101 into the graft source 300. The resection guide 400 can include a resection guide body 402 that is configured and adapted to abut at least a portion of the graft source 300. The resection guide body 402 can define an inner surface that can be contoured to match a particular outer surface of the graft source 300 so that the resection guide 400 can only fit over the that particular outer surface of the graft source 300.

The resection guide 400 defines a plurality of slots that are each configured to receive the cutting tool 101 to guide the movement of the cutting tool 101 toward the graft source 300. In the depicted embodiment, the resection guide 400 can define a first slot 410, a second slot 412, a third slot 416, and a fourth slot 418 that are spaced from one another. Each of the slots 410, 412, 416, and 418 extend through the resection guide body 402. The resection guide 400 can be configured so that the slots 410, 412, 416, and 418 are substantially aligned with the predetermined resection axes 310, 312, 314, 316, and 318 when the resection guide 400 is placed over the graft source 300. For example, the first slot 410 can be substantially aligned with the first resection axis 310 when the resection guide 400 is placed over the graft source 300. The second slot 412 can be substantially aligned with the second resection axis 312 when the resection guide 400 is placed over the graft source 300. The third slot 414 can be substantially aligned with the third resection axis 314 when the resection guide 400 is placed over the graft source 300. The fourth slot 416 can be substantially aligned with the fourth resection axis 316 when the resection guide 400 is placed over the graft source 300. The fifth slot 418 can be substantially aligned with the fifth resection axis 318 when the resection guide 400 is placed over the graft source 300.

In addition to the slots, the resection guide 400 can further define one or more drill holes 406 that are configured and sized to receive at least one drill bit or any other apparatus that is capable of making anchoring locations 303, such as a hole or bore, in the graft source 300. In operation, the drill bit can be inserted through some or all of the drill holes 406 to make a hole in the graft source 300. The anchoring locations formed in the graft source 300 are configured and sized to receive an anchor, such as screw, rivet, nail or an suitable bone fixation device. The anchoring locations 303 can correspond to openings formed in a fixation member, such as plate, such that the anchor can be inserted through fixation member openings into the respective anchoring locations 303 in the graft source 300, as discussed below.

The resection guide 400 can further define one or more fastener holes 407 that are configured and sized to receive a fastener, such as a pin, a wire, or a screw. The fastener can be inserted through the fastener holes 407 and into the graft source 300 to temporarily couple the resection guide 400 to the graft source 300. The resection guide 400 can be coupled to the graft source 300 by inserting fasteners through the fastener holes 407. Then, the cutting tool 101 can be inserted sequentially through the slots 410, 412, 416, and 418 and advanced into the graft source 300 to so as to cut and harvest the graft portions 304, 306, and 308. A drill bit can inserted in the drill holes 406 to form anchoring locations 303 (not shown) in the graft source portions 304, 306, and 308 The resection guide 400 can then be decoupled from the graft source 300 by removing the fastener from the fastener holes 407 and the graft source 300.

With reference to FIG. 1F, the graft portions 304, 306, and 308 can then be placed in the void 14 (FIG. 1C) in order to replace the tissue portion removed from the tissue body 10. The graft portions 304, 306, and 308 can then be coupled to each other to form the graft 320. Any suitable fixation member 322, such as a fixation plate 324, and a plurality of anchors, such as screws can be used to couple the graft portions 304, 306, and 308 can together to form the graft 320. The graft 320 can be a bone graft, and can be connected to the tissue body 10 using the fixation member 322, such as the fixation plate 324.

In an embodiment, the fixation member 322 can be configured as a bone fixation implant. The fixation member 322 can be bent so that its contour matches the contour of the tissue body 10 and the interconnected graft portions 304, 306, and 308. For instance, the fixation member 322 can be countered along the tissue portion 12a, the graft 320 and tissue portion 12b. Further, the fixation member 322 defines one or more holes 326 that are configured to receive a anchors discussed above. The holes 326 can be threaded holes or partially threaded depending on the selected anchor type. When the fixation member 322 is placed against the tissue body 10 and the graft portions 304, 306, and 308, one or more anchors can be inserted through at least one fastener hole 326 and into anchoring locations 22 in the tissue body 10 or the anchoring locations 303 formed in the graft 320 so as to couple the graft portions 304, 306, and 308 to one another and to couple the graft 320 to the tissue body 10. The fixation member 322 can be formed from a variety of biocompatible materials, such as cobalt chromium molybdenum (CoCrMo), titanium, and titanium alloys, stainless steel, ceramics, or polymers such as polyetheretherketone (PEEK), polyetherketoneketone (PEKK), and bioresorbable materials. A coating may be added or applied to the bone fixation implant 410 to improve physical or chemical properties or to provide medications. Examples of coatings include plasma-sprayed titanium coating or Hydroxyapatite. In accordance with an alternative embodiment, the fixation member 322 can be patient specific bone fixation plate.

Referring to FIGS. 2 and 3A-3D, 5A and 5B, a method of making a patient specific surgical resection guide, for instance any of the resection guides 100, 200 and/or 400 described above disclosure or any other suitable resection guide. The method can include all or some of the steps schematically represented as steps A, B, C, D, E, and F in FIG. 2, some of which are carried out using one or more computing devices, or computers 530 running suitable software used to manipulate or edit images and or three-dimensional models. In accordance with the embodiment illustrated in FIG. 2, the method of making a patient specific surgical guide can include in step A obtaining a physical model of a tissue body and a fixation member, for instance fixation member 322. Step B can include scanning the physical model of the tissue body and the fixation member using a scanning and or mapping machine 508. Step C can include creating a virtual three-dimensional model of the physical model and the fixation member on a computer 530. Step D can include creating a virtual three-dimensional model of the fixation member applied to the tissue body in an intra- or post-operative configuration. Intra- or post-operative configuration means the desired or intended shape of the tissue body and fixation member when the tissue body 10 has been surgically reconstructed with graft an fixation member. Step E can include creating a virtual three-dimensional model of a resection guide based on the intra- or post-operative virtual three-dimensional model of the tissue body and the fixation member. Step F can include making a surgical resection guide based on the virtual three-dimensional model of the resection guide.

Figure 2:
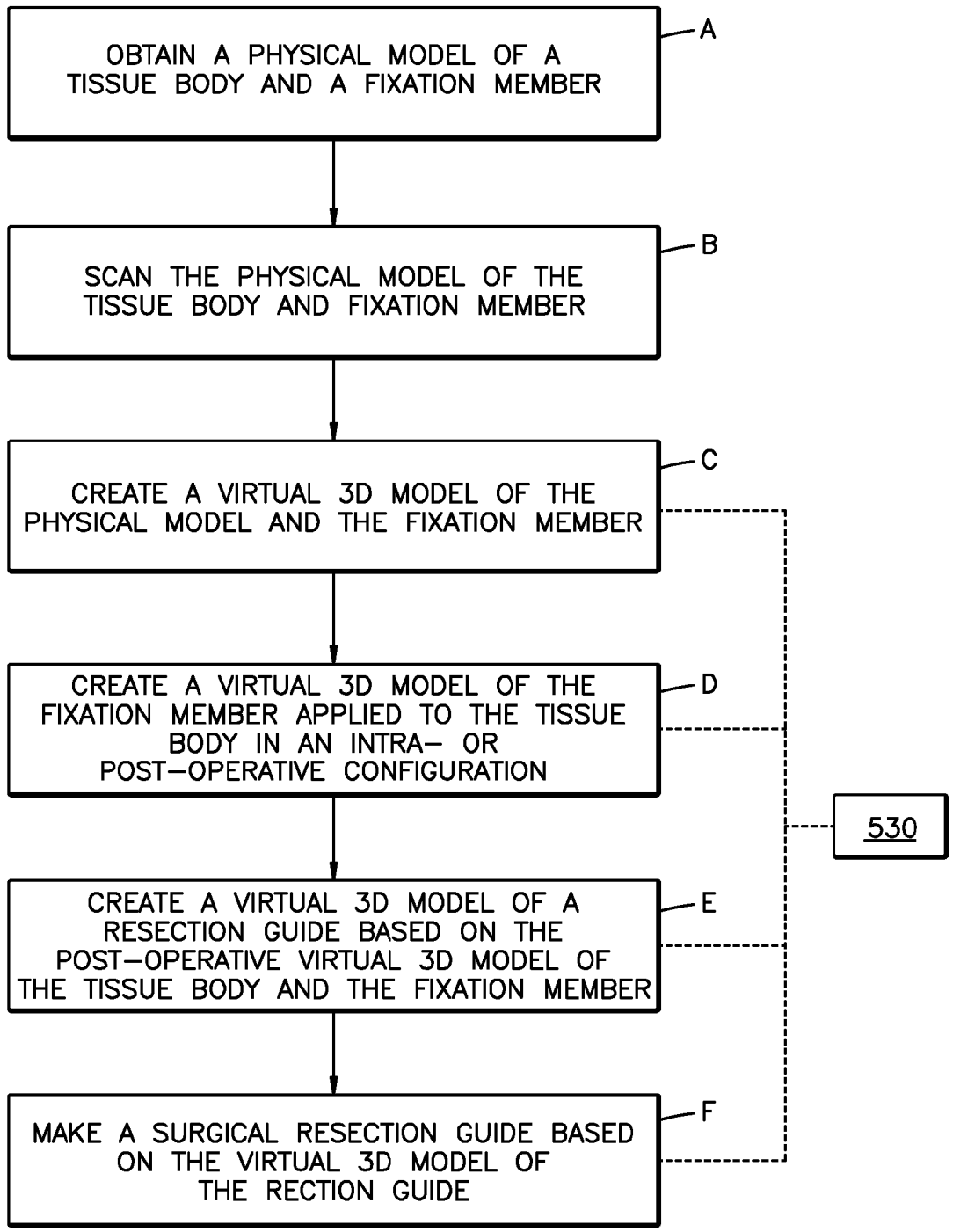
FIG. 2 is a diagram illustrating the method of making any of the resection guides shown in FIGS. 1A, 1B, and 1E, in accordance with an embodiment of the present disclosure.
Figure 3C:
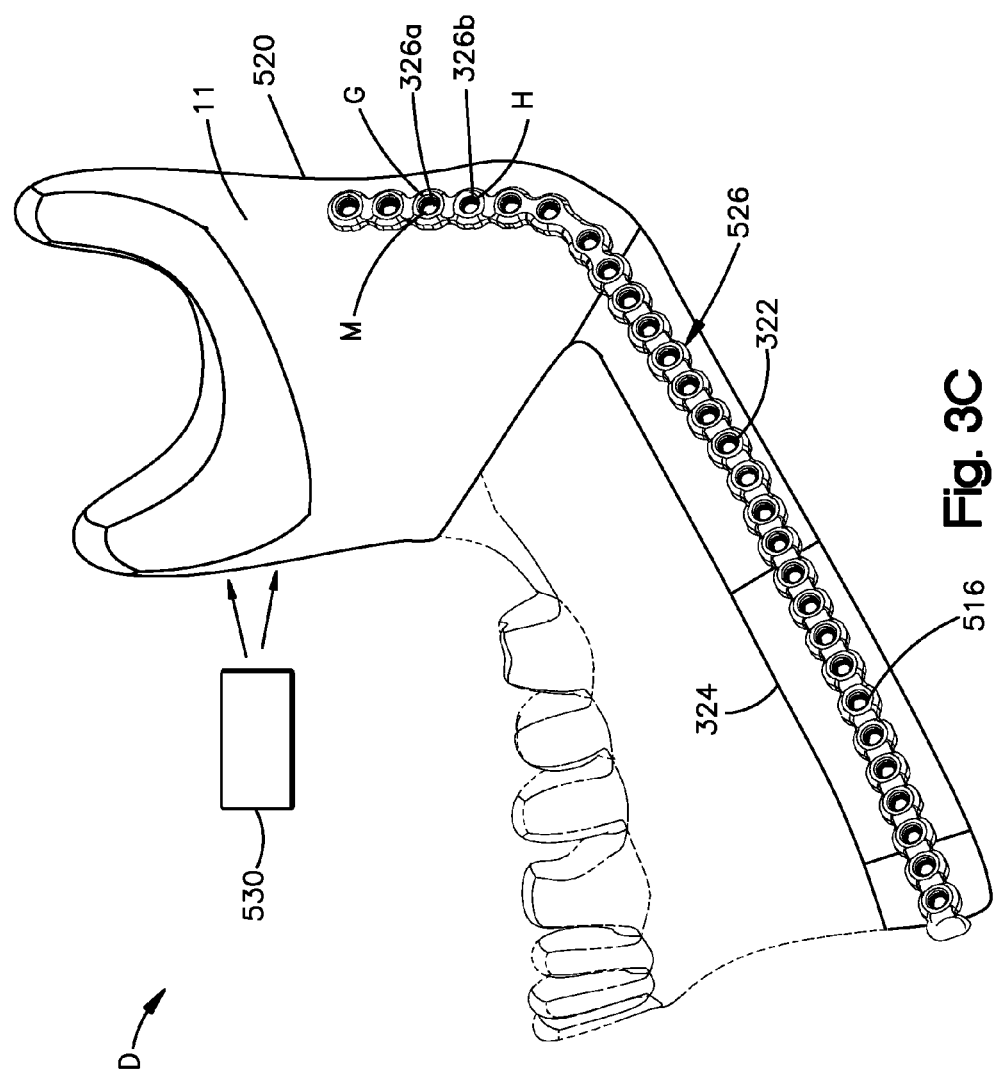
FIG. 3C illustrates a virtual three-dimensional model of a resection guide fixation member applied to the tissue body in an intra- or post-operative configuration.

Referring FIGS. 2 and 3B, in step A the user obtains a physical model 500 of the tissue body 10. The tissue body 10 can be a native tissue body or a reconstructed tissue body. The physical model 500 of the tissue body 10 can be created by scanning the tissue body 10 using any suitable technology and then forming a three-dimensional model based on the scanned data. For instance, a virtual three-dimensional model 510 of the tissue body 10 can be obtained by scanning the tissue body 10 using any suitable technology, such as CT scan machine, laser scanning machine, optical scanning machine, MRI machine, and coordinate measure machine. In an embodiment, a scanning machine can be used to scan a tissue body 10 so as to obtain scanned data of the tissue body 10. The scanned data is then downloaded or transferred to a computer in electrical communication with the scanning machine. For instance the scanned data can be transmitted wirelessly or via hard connection through a LAN, WAN or any suitable communications network to the computer. In the computer, a virtual three-dimensional model 510 of the tissue body 10 is created using a computer running suitable software capable of processing and editing, or manipulating images and/or image data. The virtual three-dimensional model 510 of the tissue body 10 is a representation of the tissue body 10 in its pre-operative condition. As further detailed below, the virtual three-dimensional model 510 of the tissue body 10 can be manipulated in accordance with a surgical plan in order to obtain a virtual three-dimensional model 520 (FIG. 3C) of the tissue body 10 in its intra- or post-operative configuration. In other words, the virtual three-dimensional model 510 can be manipulated such that the model represents the desired or intended shape and configuration of the tissue body 10 when the resected tissue has be replaced by the graft 320. The virtual three-dimensional model 520 of the tissue body 10 is downloaded or transferred via a communications network to a manufacturing machine or machines. Then, using the virtual three-dimensional 520 model of the tissue body 10, the manufacturing machine can create a physical model 500 (FIG. 3A) of the tissue body 10 in its intra- or post-operative condition. For instance, a rapid prototyping device or process can be used to create the physical model 500 of the tissue body 10 using the virtual three dimensional model of the tissue body 10. In rapid prototyping manufacturing processes, a virtual design, such as a computer aided design model, is transformed into a physical model. Examples of rapid prototyping devices and processes include, but are not limited to, selective laser sintering (SLS), fused deposition modeling (FDM), stereolithography (SLA), and 3D printing. A computer numerical control (CNC) machine can also be used to create the physical model 500 of the tissue body 10 in its pre-operative or post-operative condition.

Once the user obtains the physical model 500 of the tissue body 10, the fixation member 322, such as a fixation plate 324 or any other bone fixation implant, can be coupled to the physical model 500. In the depicted embodiment, the fixation plate 324 can bent to conform to the shape of the physical model 500. That is, the fixation member 322, such as the fixation plate 324, can be shaped in accordance with a planned post-operative shape. The fixation plate 324 can be coupled to the physical model 500 at the same location and in the same orientation on the physical model 500 as it would be placed on the tissue body 10. One or more markers 502 can be at least partially inserted at least one of the holes 326 of the fixation member 322 to mark the location and angulation of that fastener hole 326. Each marker 502 can include a handle 504 and a rod 506 that extends from the handle 504. At least a portion of the rod 506 can be configured and sized to be received by one of the holes 326. The rod can define a length and in some embodiments, Some markers 502 can have rods 506 with shorter lengths than others. The markers 502 with the shorter length rods 506 can be positioned between markers 502 with longer rods 506 to accommodate the maximum number of markers 502 in the fastener holes 326.

With reference to FIGS. 4A and 4B, the fixation member 322 can include a fixation member body 321. The fixation member body 321 extends between a first end 321a and a second end 321b opposite the first end 321a along a longitudinal direction L. The fixation body 321 defines an outer surface 323 and an inner surface 325 spaced from the outer surface 323 along a transverse direction T that is transverse to the longitudinal direction L. The inner surface 325 is configured so contour to the surface of the graft source or tissue body 10. The fixation member 322 has a thickness defined as the distance between the outer surface 323 and the inner surface 325. The fixation member body 321 define a plurality of holes 326 that extend through the fixation member body 321 along a central hole axis X. The holes 326 space apart from each other along longitudinal direction L. Each hole 326 is configured and sized to receive at least an anchor therethrough. The holes 326 can be as threaded or partially threaded. The holes 326 can be configured in any suitable manner or orientation to receive an anchor therein. The central hole axis X can thus be angulated respect to the direction T. In an embodiment, the central axes X of some or all of the holes 326 can be angularly offset relative to the direction T. The fixation member 322 is configured to be bent to conform to the shape of a portion of the tissue body 10 or a portion of the physical model 500 of the tissue body as shown in step A of FIG. 3A. Before bending the fixation member 322, small screw inserts (not shown) can be placed in the holes 326 to help maintain the shape of the holes 326 during the bending process. Furthermore, the fixation member 322 is generally not bent or deformed at positions where the holes 326 are located to avoid, or at least minimize significantly changing the shape of the holes 326 during bending.

The markers 502 can be used to accurately create the holes 326 in a virtual three-dimensional model of the fixation member 322. As discussed above in step A, markers 502 can be inserted through the holes 326 after the fixation member 322 has been bent to conform to the shape of at least a portion of the physical model 500 and coupled to the physical model 500. A portion of the marker 502, such as a portion of the rod 506, can be inserted in one of the holes 326 such that that rod 506 extends along the respective central hole axis X. Hence, the rod 506 can be elongate along the central hole axis X of one of the holes 326 when at least a portion of the rod 506 is inserted in that specific hole 326. Accordingly, markers 502 can be inserted in one or more holes 326 to identify the angulation of the respective hole 326.

Referring to FIG. 2, in step B the physical model 500, the fixation member 322, and the markers 502 can be scanned using any suitable scanning or imaging technology as described above to obtain scanned image data for the physical model 500, the fixation member 322, and the markers 502. For instance a scanning machine can be used to scan the physical model 500, the fixation member 322, and the markers 502, and using the scanned image data can be used, via a computer 530 to create a virtual three-dimensional model 512 of the physical model 500, the fixation member 322, and the markers 502. In accordance with an alternative embodiment, only physical model 500 and the fixation member 322 are scanned, and a virtual three-dimensional model is created of the physical model 500 and the fixation member 322 such that the markers 502 are not scanned. In a further embodiment, only the fixation member 322, which has been shaped in accordance with a planned intra- or post-operative configuration, is scanned. In particular, the fixation member 322 can be bent to a shape to its planned intra- or post-operative shape and then scanned to obtained the scanned image data.

Referring to FIGS. 2 and 3B, in step C, once the three-dimensional image of the fixation member 322 coupled to the physical model 500 is obtained with the scanning machine, the scanned image data is loaded onto a computer 530 to create a virtual three-dimensional model 512 of the physical model 500, the fixation member 322, and the markers 502. Alternatively, a virtual three-dimensional model of at least the fixation member 322 can be created with the computer 530 without the need of scanned image data of the physical model 500 of the fixation member 322. The computer 530 can include a processor and a non-transitory computer readable storage medium configured to store data, such as scanned image data, and suitable software. The computer 530 may be local, for instance in the same general area as the scanning machine, or remote and the scanned image data is transferred to the computer 530 via a communications network. Thus the obtain or stored scanned image data can be manipulated by a user via software running on the computer that is local to the scanning machine and/or surgery location or remote to the scanning machine and/or surgery location. For example, the scanned image data can be manipulated remotely by the surgeon who will be performing the surgery. The virtual three-dimensional model 512 is typically composed of data in different formats. For instance, the three-dimensional model 512 can contain data in a Standard Tessellation Language (STL) format. Regardless of the data format, the virtual three-dimensional model 512 includes data that maps and represents the shape, contour, and size of at least the physical model 500 and the fixation member 322 as coupled to the physical model 500.

Continuing with reference FIGS. 2 and 3B, in step C the virtual three-dimensional model 512 can include data representing the markers 502 position in the fixation members 322 so as to enhance the accuracy of the orientation of the holes 326 of the fixation member 322. With the visual representation of the markers 502, the user can better determine the orientation of the holes 326 of the fixation member 322. As discussed above with respect to FIGS. 4A and 4B, the markers 502 can help determine the angulation of the hole 326 with respect to the transverse on T of the fixation member 322.

Using the scanning process in step B, the location of the opposed ends 327 of each hole 326 can be obtained. However, the path of each hole 326 from a first hole end 327 to a second hole end 329 may not be necessarily obtained by the scanning process described in step B. Hence, the virtual three-dimensional model 512 can be manipulated to virtually create each of the holes 326 virtual model of the fixation member 322. To do so, the central hole axis X can be developed in the virtual model so to extend through the a center of the first hole end 327 and the center of the second hole end 329. Then, the hole 326 is created so that it has a path along the previously drawn central axis X' of that particular hole 326. This process does not entail the use of the markers 502. Alternatively, the visual representation of the markers 502 can be used obtain a more accurate path for the holes 326. To do so, the central axis X' is drawn from the second hole end 329 to an end 507 of the rod 506 that is attached to the handle 504. Then, the hole 326 that follows the central axis X is created in the virtual three-dimensional model 512. This process can be repeated for each hole 326.

In step C, the virtual three-dimensional model 512 can include models of each component. That is, the virtual three-dimensional model 512 can include a virtual three-dimensional model 514 of the physical model 500, a virtual three-dimensional model 516 of the fixation member 322, such as the fixation plate 324, and a virtual three-dimensional model 518 of the markers 502. The virtual three-dimensional models 512 (or any virtual model described herein) can be manipulated by a user using conventional software typical in the art. For example, a software program that is configured to process and edit images, sold under the trademark PROPLAN CMF® by Synthes, may be used to process and manipulate the virtual models obtain from the scanning machine 508. The software allows the user to analyze the tissue body 10 and pre-operatively plan the patient's surgery including the shape and design of a resection guide, such as a resection guide 600 discussed below.

Referring to FIGS. 2 and 3C, in step D, the virtual three-dimensional model 520 of the tissue body 10 can be manipulated into the intra- or post-operative shape and configuration in accordance with a planned surgical procedure. Specifically, the virtual three-dimensional model 516 of the fixation member 322 can be imported into a previously obtained three-dimensional model 520 of the tissue body 10, and manipulated using a computer create a virtual three-dimensional model 520 of the tissue body 10 in the intra- or post-operative shape and configuration. In other words, using the virtual three-dimensional model 520 of the tissue body 10, the user may pre-plan a surgery, such as a mandibular reconstruction surgery, in the computer 530 using a suitable software such as the software sold under the trademark PROPLAN CMF® by Synthes. In the computer 530, the virtual three-dimensional model 516 of the fixation member 322 can be coupled to the virtual three-dimensional model 520 of the tissue body 10 in the intra- or post-operative configuration in accordance with a predetermined surgical plan as discussed in detail above with respect to FIG. 1F. Thus, the virtual three-dimensional model 516 of the fixation member 322 can be aligned with the virtual three-dimensional model 520 of the tissue body 10 according to a desired surgical plan. As discussed above, the three-dimensional model 520 can represent a native tissue body 10 or a reconstructed tissue body 10 that includes the graft 320. The virtual three-dimensional model 516 of the fixation member 322 coupled to the three-dimensional model 520 of the tissue body 10 are collectively referred to as the virtual three-dimensional model 526.

Figure 3D:
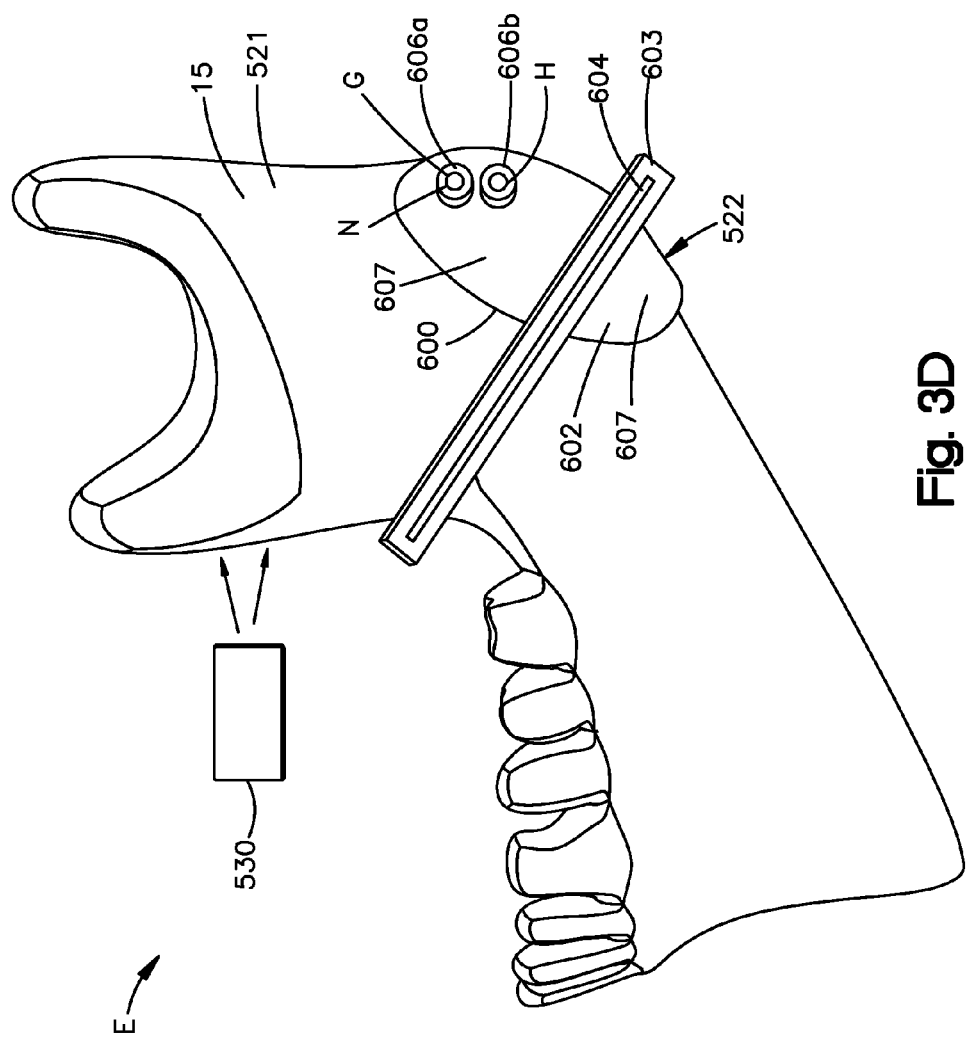
FIG. 3D illustrates a virtual three dimensional model of a resection guide and a tissue body, in accordance with an embodiment of the disclosure.

Referring to FIGS. 2 and 3D, in step E, a virtual three-dimensional model 522 of a resection guide 600 can be created and designed based on the virtual three-dimensional model 526 of the fixation member 322 coupled to the tissue body 10. Thus, the resection guide 600 (or any other suitable resection guide) can be designed and manufactured based on the virtual three-dimensional model 526 of the fixation member 322 coupled to the virtual model 520 of the tissue body 10. In accordance with an alternate embodiment, the virtual three-dimensional model 522 of the resection guide 600 can be created using a virtual three-dimensional model 521 of the tissue body 10 that has been previously obtained via a scanning machine. The virtual three-dimensional model 521 of the tissue body 10 can be substantially identical to the virtual three-dimensional model 520 of the tissue body 10 used in step D. However, in some embodiments, the virtual three-dimensional model 521 of the tissue body 10 represents the tissue body 10 in a pre-operative shape or condition.

Continuing with reference to FIGS. 2 and 3D, in step E a virtual three-dimensional model 522 of the resection guide 600 is can be configured to or designed to allow a surgeon to guide movement of the cutting tool 101 toward the tissue body 10, for instance when the resection guide is formed as detailed below. In the depicted embodiment, the resection guide 600, or the model of the resection guide, can include a resection guide body 602 that is configured to abut at least a portion of the tissue body 10. The resection guide body 602 can define at least one slot 604 that extends through the resection guide body 602. The slot 604 can be configured and sized to receive the cutting tool 101, and guide the cutting tool 101 toward the tissue body 10 when the resection guide 600 is coupled to the tissue body 10, as represented in a three-dimensional virtual model. In addition to the slot 604, the resection guide 600 can define one or more drill holes 606 that are each configured and sized to receive a drill bit or any other apparatus capable of making holes or anchoring locations in the tissue body 10. Each of the drill holes 606 can extend through the resection guide body 602. In addition to the drill holes 606, the resection guide 600 can define one or more fastener holes 607 that are each configured and sized to receive a fastener such as a screw. Each of the fastener holes 607 can extend through the resection guide body 602. At least one fastener can be inserted through each fastener hole 607 and into the tissue body 10 to couple the resection guide 600 to the tissue body 10.

Continuing with FIGS. 2 and 3D, in step E, the virtual three-dimensional model 522 of the resection guide 600 can be designed such that the location and orientation of the drill holes 606 in the virtual three-dimensional model 522 relative to the tissue body 10 are substantially aligned with the location and orientation of the same number of holes 326 of the fixation member 322. For instance, as show in FIG. 3C, in step C, the fixation member 322 includes first hole 326 and a second hole 326b positioned at a location and orientation G and H, respectively, relative to the tissue body 10. Accordingly, the virtual three-dimensional model 522 of the resection guide 600 can be designed, for example in the computer 530, such that at least one hole 606a and second hole 606b has substantially the same location and orientation relative to the tissue body 10 as one of the holes 326, for instance holes 326a and 326b, of the fixation member 322, relative to the location and orientations G and H on the tissue body 10. The location G can be referred to as the first position relative to the virtual three-dimensional model 520, and the location identified H can be referred to as the second position relative to the virtual three-dimensional model 520. The holes 326a and 326b are located and oriented relative to the tissue body 10 such that the insertion of anchors through the holes 326a and 326b into the anchor locations do not impinge upon nerves of the tissue body 10. Also, the holes 326 are located and oriented relative to the tissue body 10 such that anchors are inserted through tissue that is not damaged or diseased.

Referring to FIG. 2, in step F, once the virtual three-dimensional model 522 of the resection guide 600 has been completed, the resection guide 600 can be made based on the three-dimensional virtual model 522 using any suitable technology, such as the rapid prototyping technology. For instance, the virtual three-dimensional model 522 of the resection guide 600 can be downloaded or transferred from the computer 530 to a machine such as a CAD/CAM manufacturing machine, or to a computer coupled to such a machine. The resection guide 600 can be made using a rapid prototyping manufacturing devices or process. In rapid prototyping manufacturing process, a virtual design, such as a computer aided design model, is transformed into a physical model or construct. Examples of rapid prototyping technologies include, but are not limited to, selective laser sintering (SLS), fused deposition modeling (FDM), stereolithography (SLA), and 3D printing, as well as a computer numerical control (CNC) machine. The manufacturing machine 532 makes the resection guide 600 out of any desired material. For example, the resection guide 600 can be partly or entirely made of a suitable polymer or metallic material. Then, the user can perform any desired surgical operation on a patient using the resection guide 600. All or some of the steps shown in FIG. 2A can be executed by a processor or a computer. In addition, all or some of the data involved in the method described above, such as the virtual models, can be stored on non-transitory computer readable storage medium to a local computer or a remote computer.

Aside from the resection guide 600, the method described above can be used to make any other suitable resection guide. For example, the resection guides 100 and 200 can be made using the method described above. It should be appreciated that all the virtual three-dimensional models mentioned in the present disclosure can be created and manipulated using a computer aided software that is run in computer 530. The method described in the present application can be used to manufacture resection guides for use in mandibular reconstruction surgery as described above. However, the method described in the present application can be used to make resection guides for use in orthognatic surgery or craniomaxillofacial surgery that may include distraction of bone segments.

Figure 5A:
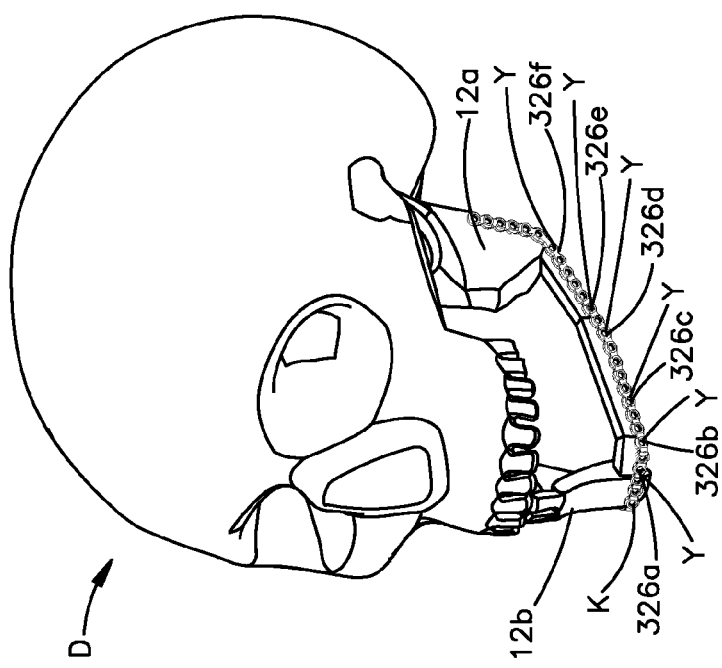
FIGS. 5A and 5B illustrate a virtual three-dimensional model of the fixation member applied to the tissue body, and a virtual three-dimensional model of a resection guide applied to the graft source, respectively, illustrating how the virtual three-dimensional model of the resection guide includes elements that correspond to the virtual three-dimensional model of the fixation member.
Figure 5B:
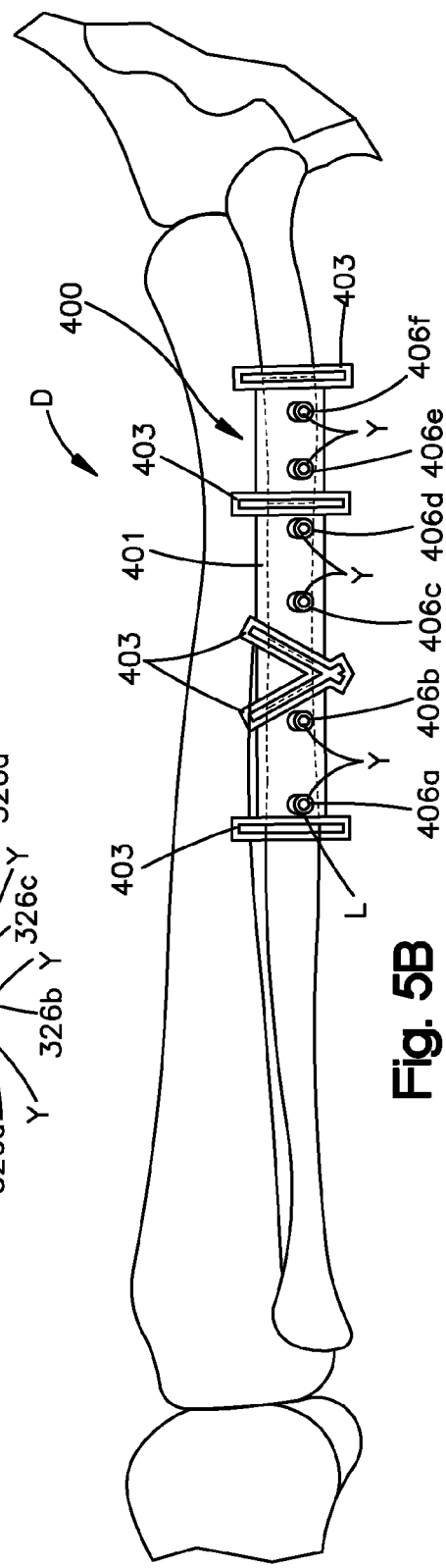

With reference to FIGS. 5A and 5B, the method described above can also be used to construct the resection guide 400 used to harvest the graft. In this method, the resection guide 400 can include one or more slots 403 and a plurality of drill holes 406a-406f. The resection guide 400 can be virtually designed so that the location and orientation of the that the drill holes 406a-f relative to the graft 320 are in substantial alignment with the fastener holes 326a-f and tissue locations Y when the graft 320 is positioned in the void 14 (FIG. 1C) and the fixation member 322 is positioned against the graft 320 and the tissue body 10. For instance, the virtual three-dimensional model 512 of the tissue body 10 is obtained as described above with respect to steps A-C discussed above and show in FIGS. 2, 3A and 3B. Then, on a virtual three-dimensional model of the tissue body 10, a first resection region 11 (FIG. 1A) and a second resection region 13 (FIG. 1A) are identified. The first resection region 11 is also referred to as the first region 11, and the second resection region 13 is also referred to as the second region 13. The virtual three-dimensional model 516 of the fixation member 322 is obtained as described above with respect to FIG. 2. The obtained three-dimensional model 516 can have a planned post-operative shape, and can define at least one first hole 326 that is configured to receive a fastener. The virtual three-dimensional model 516 of the fixation member 322 is processed (in a processor) so as to obtain the virtual three-dimensional model 516 of the fixation member 322, such that a central axis of the at least one first hole 326a is substantially aligned with a first target location K of the at the second tissue portion 12a of the tissue body. The virtual three-dimensional model 401 of the resection guide 400 is created by, for example, scanning the resection guide 400 as described above in steps B and C of FIG. 2. The virtual three-dimensional model 401 of the resection guide 400 can be processed (in a processor) so as to couple the virtual three-dimensional model 401 of the resection guide 400 to the virtual three-dimensional model 301 of the graft portion disposed between at least two cutting guides 403. The graft portion can be graft portion 304, graft portion 306, graft portion 308, or a combination thereof. Thus, the graft portion can be the graft 320. The graft portion, such as the graft 320, can be sized to fit in the second region 13 or void 14. The virtual three-dimensional model 401 of the resection guide 400 can be processed via a processor on a computer so as to couple the virtual three-dimensional model 401 of the resection guide 400 to the virtual three-dimensional model 301 of the graft portion, such that the central axis of one of the drill holes 406 is substantially aligned with one of the target locations L of the graft source. At least one of the target locations L substantially coincides with the target location K when the graft 320 is positioned in the void 14.

Figure 6:
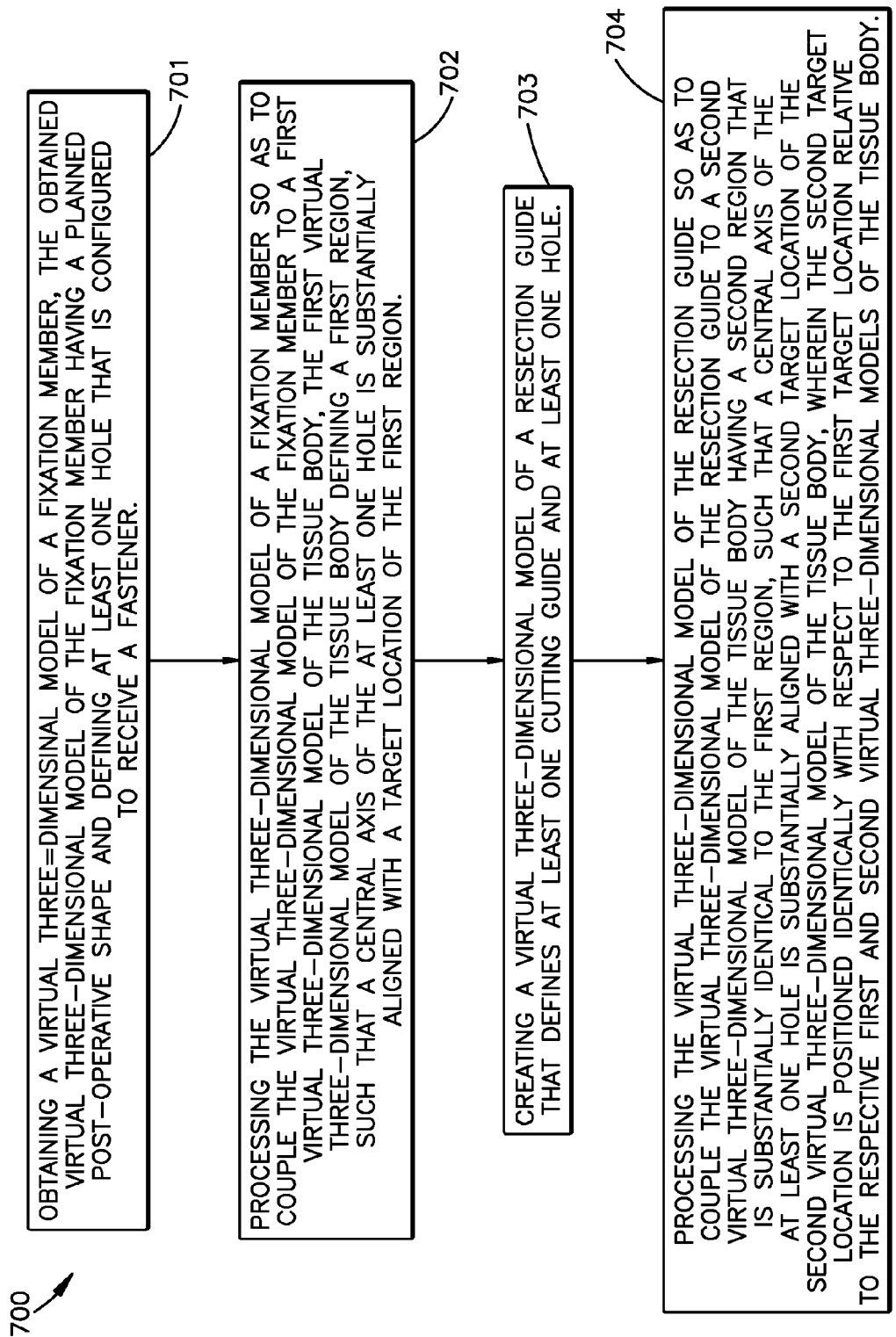
FIG. 6 is a flowchart that describes a method of making a resection guide in accordance with an embodiment of the present disclosure.

With reference to FIG. 6, a method 700 of making a resection guide can include steps 701, 702, 703 and 704. Step 701 includes obtaining a virtual three-dimensional model 516 of a fixation member 322, wherein the obtained virtual three-dimensional model 516 of the fixation member 322 has a planned post-operative shape and defines at least one hole 326 that is configured to receive a fastener. Step 702 includes processing the virtual three-dimensional model of the fixation member 322 so as to couple the virtual three-dimensional model 516 of the fixation member 322 to a first virtual three-dimensional model 520 of the tissue body 10, the first virtual three-dimensional model 520 of the tissue body 10 defining a first region 11, such that a central axis X of the at least one hole 326 is substantially aligned with a first target location M of the first region 11. The first region 11 can correspond to the tissue portion 12b. Step 703 includes creating a virtual three-dimensional model 522 of a resection guide 600 that defines at least one cutting guide 603 and at least one hole 606. Alternatively, step 703 includes creating a virtual three-dimensional model 522 of a guide 600, such as a positioning guide or a drill guide, that defines at least one hole 606. Step 704 includes processing the virtual three-dimensional model 522 of the resection guide 600 so as to couple the virtual three-dimensional model 522 of the resection guide 600 to a second virtual three-dimensional model 521 of the tissue body 10 having a second region 13 that is substantially identical to the first region 11, such that a central axis of the at least one hole 606 is substantially aligned with a second target location N of the second virtual three-dimensional model 521 of the tissue body 10, wherein the second target location N is positioned identically with respect to the first target location M relative to the respective first and second virtual three-dimensional models 520, 521 of the tissue body 10.

The second processing step 704 can further include aligning the cutting guide 603 with a preoperatively planned interface between the first region 11 the second region 13 of the tissue body 10. The obtaining step 701 can further include scanning the fixation member 322 to obtain an image of the fixation member 322, transferring via communication network, the image data to a computer and manipulating the image of the fixation member 322 to define the at least one hole 326 of the fixation member 322 in the virtual three-dimensional model 516 of the fixation member 322. The manipulating step includes identifying the central axis X of the at least one hole 326. The method can further include constructing the resection guide 600 identical to the virtual three-dimensional model 522 of the resection guide 600 using a rapid prototyping manufacturing process. The step of constructing the resection guide 600 can include transferring the virtual three-dimensional model 522 of the resection guide 600 from the computer to a manufacturing machine 532.

The obtaining step 701 can include scanning the fixation member 322 using a scanning machine 508. The obtaining step 701 can include scanning the fixation member 322 using any one of the following scanning machines, namely: CT scan machine, laser scanner, optical scanner, MRI machine, or coordinate measure machine. The obtaining step 701 can further include coupling the fixation member 322 to a physical model 500 of the tissue body 10. The obtaining step 701 can further include bending the fixation member to the post-operative shape. The obtaining step 701 can further include inserting at least a portion of a marker 502 into the at least one hole 326 of the fixation member 322 to identify a path of the at least one hole 326 relative to a thickness of the fixation member 322. The obtaining step 701 can further include scanning the physical model 500 of the tissue body 10, the marker 502 that is inserted into at least one hole 326 of the fixation member 322, and the fixation member 322 that is coupled to the physical model 500 of the tissue body 10.

The processing step 704 can include manipulating via a processor, according to software stored in a computer readable medium, the virtual three-dimensional model 522 of the resection guide 600 so that the resection guide 600 is contoured to fit over a particular portion of the virtual the second virtual three-dimensional model 521 of the tissue body 10. All or some of the steps shown in FIG. 6 or described above can be executed by a processor running on a computer. The virtual three-dimensional models described in the present disclosure can be stored on a non-transitory computer readable storage medium. The processor and the computer readable storage medium can be part of the same computer or different computers.

With reference to FIG. 6, a method 800 of making a patient specific surgical resection guide 600 can include the steps 801, 802, and 803. The step 802 includes processing a virtual three-dimensional model 516 of a fixation member 322 so as to couple the virtual three-dimensional model 516 of the fixation member 322 to a first virtual three-dimensional model 520 of the tissue body 10, the first virtual three-dimensional model 520 of the tissue body 10 defining a first region 11, such that a central axis X of the at least one hole 326 is substantially aligned with a first target location M of the first region 11. The step 802 includes creating a virtual three-dimensional model 522 of a resection guide 600 that defines at least one cutting guide 603 and at least one hole 606. Alternatively, the step 802 includes creating a virtual three-dimensional model 522 of a guide, such as a positioning guide or a drill guide, that defines at least one hole 606. The step 803 includes processing the virtual three-dimensional model 522 of the resection guide 600 so as to couple the virtual three-dimensional model 522 of the resection guide 600 to a second virtual three-dimensional model 521 of the tissue body 10 having a second region 13 that is substantially identical to the first region 11, such that a central axis X of the at least one hole 326 is substantially aligned with a second target location N of the second virtual three-dimensional model 521 of the tissue body 10, wherein the second target location N is positioned identically with respect to the first target location M relative to the respective first and second virtual three-dimensional models 520, 521 of the tissue body 10.

Figure 7:
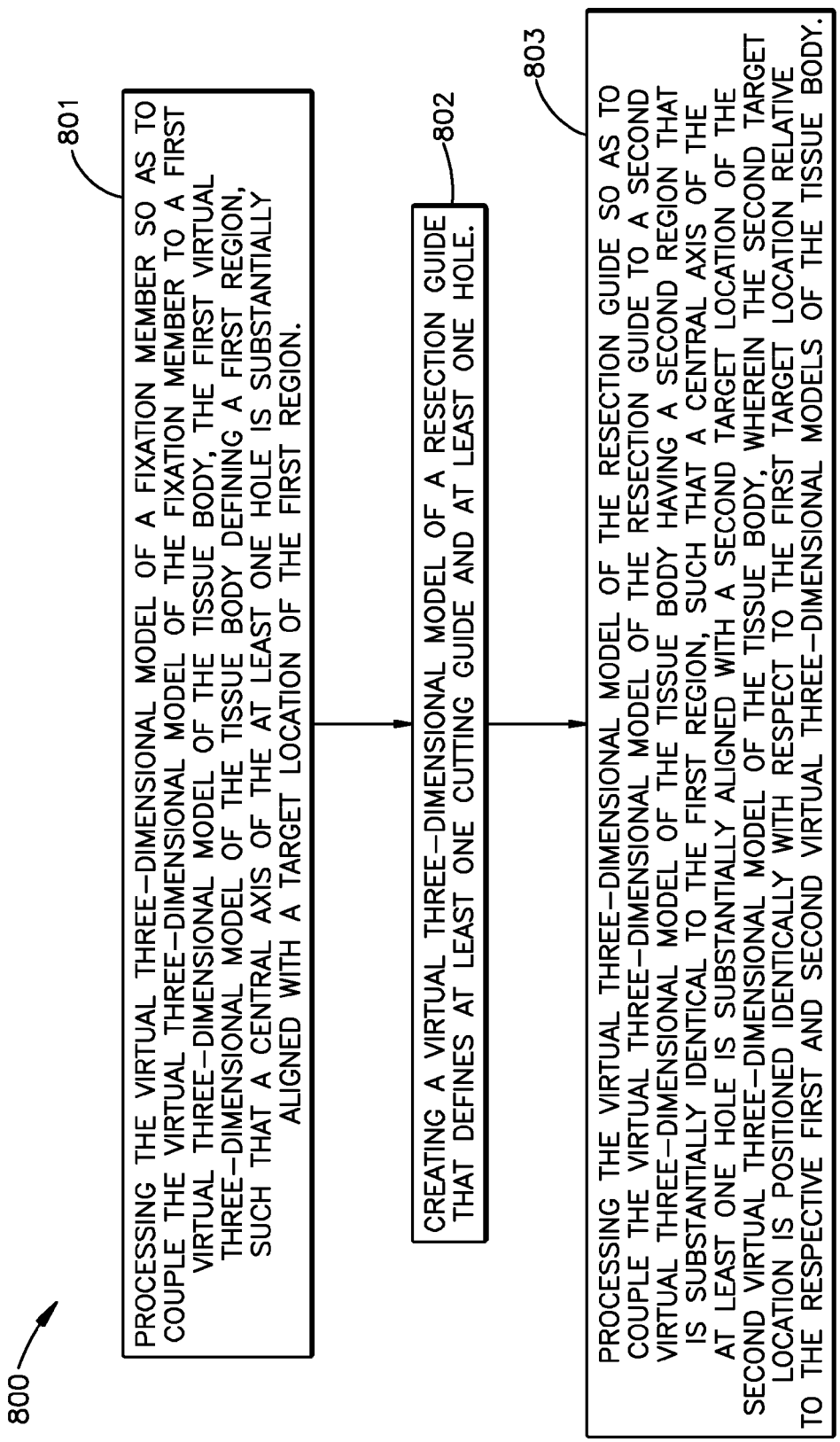
FIG. 7 is a flowchart that describes a method of making a resection guide in accordance with another embodiment of the present disclosure.

In accordance with an alternate embodiment, the method 800 illustrated in FIG. 6 can further include the step obtaining the virtual three-dimensional model 516 of the fixation member 322 in a computer 530. The obtaining step can include scanning the fixation member 322 using a scanning machine 508. The obtaining step can further include scanning the fixation member 322 using any of the following scanning machines, namely CT scan machine, laser scanner, optical scanner, MRI machine, or coordinate measure machine. The method illustrated in FIG. 4 can further include constructing the resection guide 600 identical to the virtual three-dimensional model 522 of the resection guide 600 using a rapid prototyping manufacturing process. The constructing step can further include transferring the virtual three-dimensional model 522 of the resection guide 600 from the computer 530 to a manufacturing machine 532 via a communications network. The obtaining step can include coupling the fixation member to a physical model of the tissue body. The obtaining step can include bending fixation member to the post-operative shape. The obtaining step can include inserting a marker into the at least one hole of the fixation member to identify a path of the at least one hole relative to a thickness of the fixation member. The obtaining step can include scanning the physical model of the tissue body, the marker that is inserted into at least one hole of the fixation member, and the fixation member that is coupled to the physical model of the tissue body. The obtaining step can include scanning the physical model of the tissue body, and the fixation member that is coupled to the physical model of the tissue body. The processing step 803 can include manipulating the virtual three-dimensional model of the resection guide so that the resection guide is contoured to fit over a particular portion of the virtual the second virtual three-dimensional model of the tissue body. All or some of the steps shown in FIG. 7 or described above can be executed by a processor as a computer.

Figure 8:
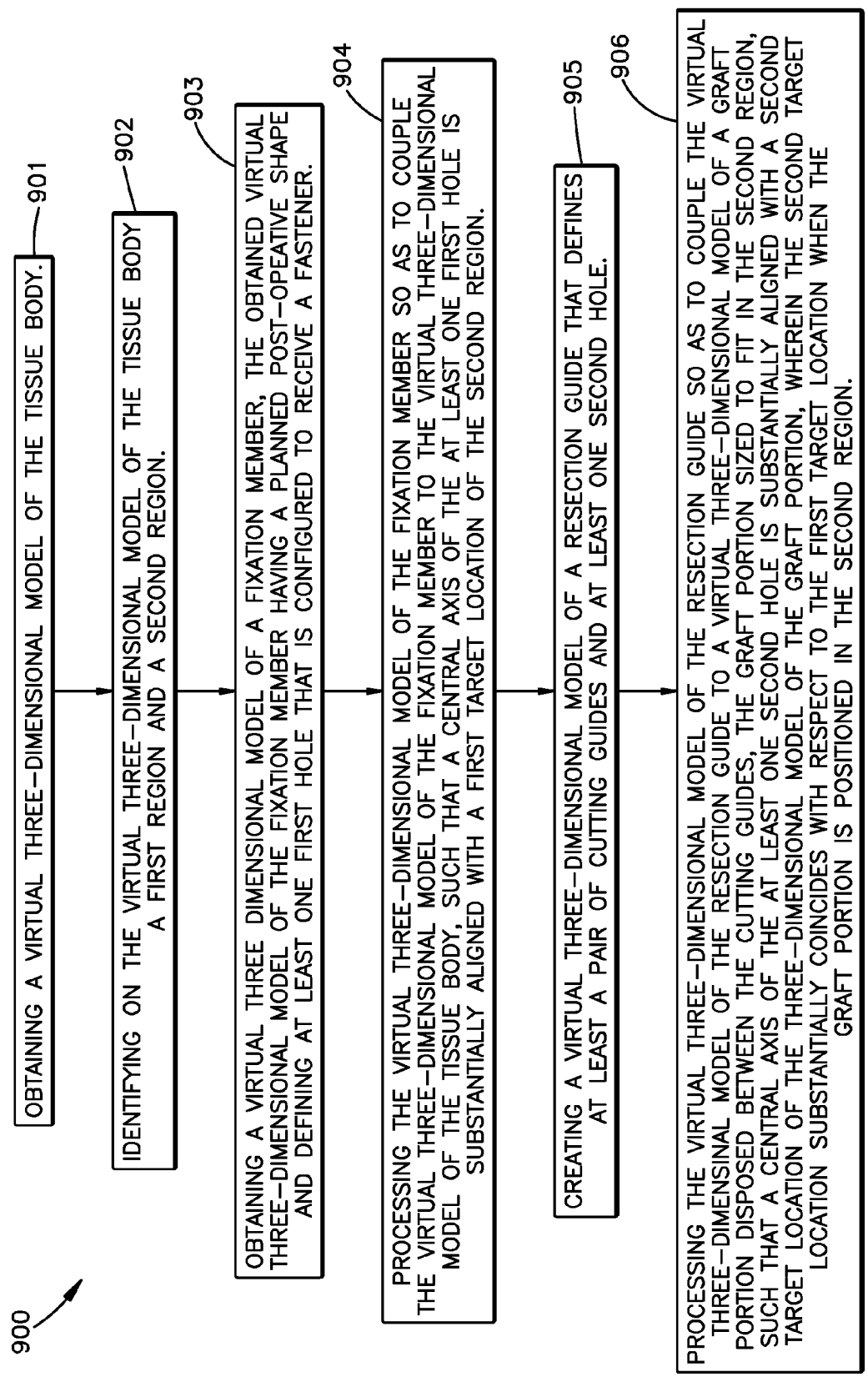
FIG. 8 is a flowchart that describes a method of making a resection guide in accordance with another embodiment of the present disclosure.

With reference to FIG. 8, a method 900 of making a patient specific surgical resection guide 600 can include the steps 901, 902, 903, 904, 905 and 906. The step 901 includes obtaining a virtual three-dimensional model 521 of the tissue body 10. The step 902 includes identifying on the virtual three-dimensional model 522 of the tissue body 10 a first retention region 11 and a second resection region 13. The first resection region 11 is also referred to as the first region 11, and the second resection region 13 is also referred to as the second region 13. The step 903 includes obtaining a virtual three-dimensional model 516 of a fixation member 322, the obtained virtual three-dimensional model 516 of the fixation member 322 having a planned post-operative shape and defining at least one first hole 326 that is configured to receive a fastener. The step 904 includes processing the virtual three-dimensional model 516 of the fixation member 322 so as to couple the virtual three-dimensional model 516 of the fixation member 322 to the virtual three-dimensional model of the tissue body 10, such that a central axis X of the at least one first hole 326 is substantially aligned with a first target location K of the second resection region 13. The step 905 includes creating a virtual three-dimensional model 401 of a resection guide 400 that defines at least a pair of cutting guides 403 and at least one second hole 406. The step 906 includes processing the virtual three-dimensional model 401 of the resection guide 400 so as to couple the virtual three-dimensional model 401 of the resection guide 400 to a virtual three-dimensional model 301 of a graft portion 320 disposed between the cutting guides 403, the graft portion 320 sized to fit in the second region 13, such that a central axis of the at least one second hole 406 is substantially aligned with a second target location L of the three-dimensional model 301 of the graft portion 320, wherein the second target location L substantially coincides with respect to the first target location K when the graft portion 320 is positioned in the second resection region 13. All or some of the steps shown in FIG. 5 or described above can be executed by a processor. The obtaining step 901 can further include scanning the fixation member to obtain an image of the fixation member, and manipulating the image of the fixation member to define the at least one first hole of the fixation member in the virtual three-dimensional model of the fixation member. The manipulating step can further include identifying the central axis of the at least first one hole. The method can further comprise the step of constructing the resection guide identical to the virtual three-dimensional model of the resection guide using a rapid prototyping manufacturing process.

It should be noted that the illustrations and discussions of the embodiments shown in the figures are for exemplary purposes only, and should not be construed limiting the disclosure. One skilled in the art will appreciate that the present disclosure contemplates various embodiments. For example, although the present disclosure refers to virtual three-dimensional models, it is envisioned that any of the virtual models described in the present disclosure can be two-dimensional. It should be further appreciated that the features and structures described and illustrated in accordance one embodiment can apply to all embodiments as described herein, unless otherwise indicated. Additionally, it should be understood that the concepts described above with the above-described embodiments may be employed alone or in combination with any of the other embodiments described above.

What is claimed is:
1. A method of making a patient specific surgical guide that is configured to guide a movement of a cutting tool toward a tissue body, the method comprising:
obtaining a virtual three-dimensional model of a fixation member, the obtained virtual three-dimensional model of the fixation member having a planned post-operative shape and defining at least one hole that is configured to receive a fastener;
processing the virtual three-dimensional model of the fixation member so as to couple the virtual three-dimensional model of the fixation member to a first virtual three-dimensional model of the tissue body, the first virtual three-dimensional model of the tissue body defining a first region, such that a central axis of the at least one hole is substantially aligned with a first target location of the first region;
creating a virtual three-dimensional model of a guide that defines at least one hole; and
processing the virtual three-dimensional model of the guide so as to couple the virtual three-dimensional model of the guide to a second virtual three-dimensional model of the tissue body having a second region that is substantially identical to the first region, such that a central axis of the at least one hole of the virtual three-dimensional model of the guide is substantially aligned with a second target location of the second virtual three-dimensional model of the tissue body, wherein the second target location is positioned identically with respect to the first target location relative to the respective first and second virtual three-dimensional models of the tissue body.

2. The method according to claim 1, wherein the creating step includes creating the virtual three-dimensional model of the guide that defines at least one cutting guide.

3. The method according to claim 2, wherein the second processing step further comprises aligning the cutting guide with a preoperatively planned interface between the second region and a resection region of the tissue body.

4. The method according to claim 1, wherein the obtaining step further comprises scanning the fixation member to obtain an image of the fixation member, and manipulating the image of the fixation member to define the at least one hole of the fixation member in the virtual three-dimensional model of the fixation member.

5. The method according to claim 4, wherein the manipulating step comprises identifying the central axis of the at least one hole.

6. The method according to claim 1, further comprising constructing the guide identical to the virtual three-dimensional model of the guide using a rapid prototyping manufacturing process.

7. The method according to claim 6, wherein the step of constructing the guide includes transferring the virtual three-dimensional model of the guide from a computer to a manufacturing machine.

8. The method according to claim 1, wherein the step of obtaining the virtual three-dimensional model of the fixation member includes scanning the fixation member using a scanning machine.

9. The method according to claim 1, wherein the step of obtaining the virtual three-dimensional model of the fixation member includes scanning the fixation member using a scanning machine selected from the group consisting of CT scan machine, laser scanner, optical scanner, MRI machine, and coordinate measure machine.

10. The method according to claim 1, wherein the step of obtaining the virtual three-dimensional model of the fixation member includes coupling the fixation member to a physical model of the tissue body.

11. The method according to claim 10, wherein the step of obtaining the virtual three-dimensional model of the fixation member further includes bending the fixation member to the post-operative shape.

12. The method according to claim 10, wherein the step of obtaining the virtual three-dimensional model of the fixation member further includes inserting a marker into the at least one hole of the fixation member to identify a path of the at least one hole relative to a thickness of the fixation member.

13. The method according to claim 11, wherein the step of obtaining the virtual three-dimensional model of the fixation member further includes scanning the physical model of the tissue body, the marker that is inserted into at least one hole of the fixation member, and the fixation member that is coupled to the physical model of the tissue body.

14. The method according to claim 1, wherein the step of processing the virtual three-dimensional model of the guide includes manipulating the virtual three-dimensional model of the guide so that the guide is contoured to fit over a particular portion of the second virtual three-dimensional model of the tissue body.

15. A method of making a patient specific surgical guide that is configured to guide a movement of a tool toward a tissue body, the method comprising:

processing a virtual three-dimensional model of a fixation member so as to couple the virtual three-dimensional model of the fixation member to a first virtual three-dimensional model of the tissue body, the first virtual three-dimensional model of the tissue body defining a first region, such that a central axis of at least one hole of the virtual three-dimensional model of the fixation member is substantially aligned with a first target location of the first region;

creating a virtual three-dimensional model of a guide that defines at least one hole; and processing the virtual three-dimensional model of the guide so as to couple the virtual three-dimensional model of the guide to a second virtual three-dimensional model of the tissue body having a second region that is substantially identical to the first region, such that a central axis of the at least one hole of the virtual three-dimensional model of the guide is substantially aligned with a second target location of the second virtual three-dimensional model of the tissue body, wherein the second target location is positioned identically with respect to the first target location relative to the respective first and second virtual three-dimensional models of the tissue body.

16. The method according to claim 15, further comprising obtaining the virtual three-dimensional model of the fixation member in a computer.

17. The method according to claim 16, wherein the step of obtaining the virtual three-dimensional model of the fixation member includes scanning the fixation member using a scanning machine.

18. The method according to claim 16, wherein the step of obtaining the virtual three-dimensional model of the fixation member includes scanning the fixation member using a scanning machine selected from the group consisting of CT scan machine, laser scanner, optical scanner, MRI machine, and coordinate measure machine.

19. The method according to claim 16, wherein the step of constructing the guide includes transferring the virtual three-dimensional model of the guide from the computer to a manufacturing machine.

20. The method according to claim 19, wherein the step of obtaining the virtual three-dimensional model of the fixation member further includes inserting a marker into the at least one hole of the fixation member to identify a path of the at least one hole relative to a thickness of the fixation member.

21. The method according to claim 20, wherein the step of obtaining the virtual three-dimensional model of the fixation member further includes scanning the physical model of the tissue body, the marker that is inserted into at least one hole of the fixation member, and the fixation member that is coupled to the physical model of the tissue body.

22. The method according to claim 15, further comprising constructing the guide identical to the virtual three-dimensional model of the guide using a rapid prototyping manufacturing process.

23. The method according to claim 15, wherein the step of obtaining the virtual three-dimensional model of the fixation member includes coupling the fixation member to a physical model of the tissue body.

24. The method according to claim 23, wherein the step of obtaining the virtual three-dimensional model of the fixation member further includes bending the fixation member to the post-operative shape.

25. The method according to claim 23, wherein the step of obtaining the virtual three-dimensional model of the fixation member further includes scanning the physical model of the tissue body, and the fixation member that is coupled to the physical model of the tissue body.

26. The method according to claim 15, wherein the step of processing the virtual three-dimensional model of the guide includes manipulating the virtual three-dimensional model of the guide so that the guide is contoured to fit over a particular portion of the second virtual three-dimensional model of the tissue body.

27. A method of making a patient specific surgical guide that is configured to guide a movement of a cutting tool toward a tissue body, the method comprising:
- obtaining a virtual three-dimensional model of the tissue body;
- identifying on the virtual three-dimensional model of the tissue body a first region and a second region;
- obtaining a virtual three-dimensional model of a fixation member, the obtained virtual three-dimensional model of the fixation member having a planned post-operative shape and defining at least one first hole that is configured to receive a fastener;
- processing the virtual three-dimensional model of the fixation member so as to couple the virtual three-dimensional model of the fixation member to the virtual three-dimensional model of the tissue body, such that a central axis of the at least one first hole is substantially aligned with a first target location of the second region;
- creating a virtual three-dimensional model of a resection guide that defines at least a pair of cutting guides and at least one second hole; and
- processing the virtual three-dimensional model of the resection guide so as to couple the virtual three-dimensional model of the resection guide to a virtual three-dimensional model of a graft portion disposed between the cutting guides, the graft portion sized to fit in the second region, such that a central axis of the at least one second hole is substantially aligned with a second target location of the three-dimensional model of the graft portion, wherein the second target location substantially coincides with respect to the first target location when the graft portion is positioned in the second region.

28. The method according to claim 27, wherein the obtaining step further comprises scanning the fixation member to obtain an image of the fixation member, and manipulating the image of the fixation member to define the at least one first hole of the fixation member in the virtual three-dimensional model of the fixation member.

29. The method according to claim 28, wherein the manipulating step comprises identifying the central axis of the at least first one hole.

30. The method according to claim 27, further comprising constructing the resection guide identical to the virtual three-dimensional model of the resection guide using a rapid prototyping manufacturing process.

* * * * *